United States Patent
Sakamaki et al.

(10) Patent No.: US 10,562,995 B2
(45) Date of Patent: Feb. 18, 2020

(54) PHOTOCURABLE COMPOSITION, DENTURE BASE, AND PLATE DENTURE

(71) Applicant: MITSUI CHEMICALS, INC., Minato-ku, Tokyo (JP)

(72) Inventors: Toshikazu Sakamaki, Ichihara (JP); Takashi Koura, Ichihara (JP); Kouya Kojima, Urayasu (JP); Hirohisa Shiode, Yokohama (JP); Mai Kimura, Ichihara (JP)

(73) Assignee: MITSUI CHEMICALS, INC., Minato-Ku, Tokyo (JP)

( * ) Notice: Subject to any disclaimer, the term of this patent is extended or adjusted under 35 U.S.C. 154(b) by 0 days.

(21) Appl. No.: 15/765,353

(22) PCT Filed: Oct. 4, 2016

(86) PCT No.: PCT/JP2016/079557
§ 371 (c)(1),
(2) Date: Apr. 2, 2018

(87) PCT Pub. No.: WO2017/061446
PCT Pub. Date: Apr. 13, 2017

(65) Prior Publication Data
US 2018/0282455 A1 Oct. 4, 2018

(30) Foreign Application Priority Data
Oct. 8, 2015 (JP) ................................. 2015-200394

(51) Int. Cl.
| | | |
|---|---|---|
| *C08F 222/10* | (2006.01) | |
| *A61K 6/08* | (2006.01) | |
| *A61C 13/01* | (2006.01) | |
| *C08F 220/20* | (2006.01) | |
| *A61K 6/083* | (2006.01) | |
| *B33Y 70/00* | (2020.01) | |
| *C08F 220/26* | (2006.01) | |
| *A61C 13/00* | (2006.01) | |
| *A61C 13/08* | (2006.01) | |
| *G03F 7/00* | (2006.01) | |
| *G03F 7/029* | (2006.01) | |
| *G03F 7/031* | (2006.01) | |

(52) U.S. Cl.
CPC .... *C08F 222/1006* (2013.01); *A61C 13/0013* (2013.01); *A61C 13/01* (2013.01); *A61C 13/08* (2013.01); *A61K 6/083* (2013.01); *B33Y 70/00* (2014.12); *C08F 220/20* (2013.01); *C08F 220/26* (2013.01); *C08F 222/10* (2013.01); *G03F 7/0037* (2013.01); *G03F 7/029* (2013.01); *G03F 7/031* (2013.01); *C08F 2222/102* (2013.01); *C08F 2222/1013* (2013.01)

(58) Field of Classification Search
CPC ................ A63B 15/00; A63B 71/0622; A63B 2071/0625; A63B 2071/0638; A63B 2071/0655; A63B 2207/02; A63B 2220/12; A63B 2220/13; A63B 2220/40; A63B 2220/803; A63B 2220/807; A63B 2225/20; A63B 2225/50; A63B 2230/06; A63B 2230/50; C08F 220/20; C08F 220/26; C08F 222/10; C08F 222/1006; C08F 2222/1013; C08F 2222/102; A63F 13/211; A63F 13/245; A63F 13/385; A63F 13/5816
See application file for complete search history.

(56) References Cited

U.S. PATENT DOCUMENTS

2008/0258345 A1 10/2008 Thomas et al.
2012/0258430 A1 10/2012 Ruppert et al.

FOREIGN PATENT DOCUMENTS

| CA | 2324794 A1 | 4/2002 |
|---|---|---|
| EP | 2042486 A1 | 4/2009 |
| JP | 06-078937 A | 3/1994 |
| JP | 09-220237 A | 8/1997 |
| JP | 2002-302523 A | 10/2002 |

(Continued)

OTHER PUBLICATIONS

International Search Report (PCT/ISA/210) dated Jan. 17, 2017, by the Japanese Patent Office as the International Searching Authority for International Application No. PCT/JP2016/079557.

(Continued)

*Primary Examiner* — Sanza L. McClendon
(74) *Attorney, Agent, or Firm* — Buchanan Ingersoll & Rooney PC

(57) ABSTRACT

Provided is a photocurable composition including a monomer component including: a monomer (X) containing, within one molecule, two aromatic rings and two (meth)acryloyloxy groups, and having an Mw of from 400 to 580, and a monomer (H) containing, within one molecule, at least one of a hydroxyl group or a carboxy group, and a (meth)acryloyloxy group, and having an Mw of from 100 to 700; and a photopolymerization initiator. The composition has a functional group value (a) of from $0.5 \times 10^{-3}$ to $2.0 \times 10^{-3}$ mol/g.

Functional group value $(a) = (n_H/M_H) \times P_H$    Formula (a)

wherein $n_H$ represents the total number of hydroxyl groups and carboxy groups contained in one molecule of the (meth)acrylic monomer (H); $M_H$ represents the Mw of the (meth)acrylic monomer (H); and $P_H$ represents the mass ratio of the (meth)acrylic monomer (H) with respect to the total amount of the (meth)acrylic monomer component.

21 Claims, No Drawings

(56) References Cited

FOREIGN PATENT DOCUMENTS

| | | |
|---|---|---|
| JP | 4160311 B2 | 10/2008 |
| JP | 2013-512695 A | 4/2013 |
| WO | 01/95862 A1 | 12/2001 |

OTHER PUBLICATIONS

Written Opinion (PCT/ISA/237) dated Jan. 17, 2017, by the Japanese Patent Office as the International Searching Authority for International Application No. PCT/JP2016/079557.

Extended Search Report issued by the European Patent Office in corresponding European Patent Application No. 16853600.1-1107 dated May 9, 2019 (8 pages).

PHOTOCURABLE COMPOSITION, DENTURE BASE, AND PLATE DENTURE

TECHNICAL FIELD

The present invention relates to a photocurable composition, a denture base, and a plate denture.

BACKGROUND ART

Conventionally, a denture base made of resin (referred to as "resin base") has been produced by a method in which a plaster mold adapted to an intraoral shape of a patient is first produced by a dental method, and then a curable resin is poured into the plaster mold, followed by curing the curable resin.

In recent years, a method has been proposed in which the intraoral shape of a patient is measured by a three-dimensional measurement and a denture base is produced based on the measured result, instead of the above described method utilizing a plaster mold, so as to reduce the number of hospital visits of patients and to allow for an efficient production of a denture base (see, for example, Patent Document 1). Further, a method has also been proposed in which a dental prosthesis is produced using a three-dimensional printer (3D printer) (see, for example, Patent Document 2).

RELATED ART DOCUMENTS

Patent Documents

Patent Document 1: Japanese Patent Application Laid-Open (JP-A) No. 6-78937
Patent Document 2: Japanese Patent (JP-B) No. 4160311

SUMMARY OF THE INVENTION

Technical Problem

One example of the method of producing a stereolithographed product, preferably, a dental prosthesis, a medical device for intraoral use, or a tooth and jaw model (hereinafter, collectively referred to as "dental prosthesis or the like") using a 3D printer is a method referred to as "stereolithography", in which a dental prosthesis or the like is produced by forming a photocurable composition into the shape of the dental prosthesis or the like, and then the resulting formed product is subjected to photocuring.

In a case in which a stereolithographed product, preferably, a dental prosthesis or the like (a denture base, in particular) is produced by stereolithography, an excellent flexural strength and flexural modulus are required for the photocurable composition after being subjected to photocuring, in view of practical use. Further, in this case, an excellent fracture toughness may sometimes be required for the photocurable composition after being subjected to photocuring.

In other words, an object of one embodiment of the invention is to provide a photocurable composition which is used in stereolithography, and which has an excellent flexural strength and flexural modulus as well as an excellent fracture toughness after being subjected to photocuring.

Another object of one embodiment of the invention is to provide: a denture base which is a cured product of the above described photocurable composition and which has an excellent flexural strength and flexural modulus as well as an excellent fracture toughness; and a plate denture including the denture base.

Solution to Problem

The present inventors have found out, as a result of intensive studies, that a photocurable composition which contains a combination of specific monomer species and in which a specific functional group value (a) is within a specific range has an excellent flexural strength and flexural modulus as well as an excellent fracture toughness after being subjected to photocuring, and that the photocurable composition is particularly suitable for the production by stereolithography of a dental prosthesis or the like (in other words, a dental prosthesis, a medical device for intraoral use, or a tooth and jaw model), thereby completing the present invention.

In other words, specific means for solving the above described problems are as follows.

<1> A photocurable composition for use in stereolithography, the photocurable composition comprising:

a (meth)acrylic monomer component comprising:

a (meth)acrylic monomer (X) that is at least one selected from di(meth)acrylic monomers not containing, within one molecule, a hydroxyl group or a carboxy group and containing, within one molecule, two aromatic rings and two (meth)acryloyloxy groups, and that has a weight average molecular weight of from 400 to 580, and a (meth)acrylic monomer (H) that is at least one selected from (meth)acrylic monomers containing, within one molecule, at least one of a hydroxyl group or a carboxy group, and a (meth)acryloyloxy group, and that has a weight average molecular weight of from 100 to 700; and a photopolymerization initiator, wherein a functional group value (a) as defined by the following Formula (a) is from $0.50 \times 10^{-3}$ mol/g to $2.00 \times 10^{-3}$ mol/g:

$$\text{functional group value } (a) = (n_H/M_H) \times P_H \quad \text{Formula (a)}$$

wherein, in Formula (a), $n_H$ represents a total number of hydroxyl groups and carboxy groups contained in one molecule of the (meth)acrylic monomer (H); $M_H$ represents the weight average molecular weight of the (meth)acrylic monomer (H); and $P_H$ represents a mass ratio of the (meth)acrylic monomer (H) with respect to a total amount of the (meth)acrylic monomer component.

<2> The photocurable composition according to <1>, wherein at least one di(meth)acrylic monomer constituting the (meth)acrylic monomer (X) contains an ether bond within one molecule.

<3> The photocurable composition according to <1> or <2>, wherein at least one di(meth)acrylic monomer constituting the (meth)acrylic monomer (X) contains from one to four ether bonds within one molecule.

<4> The photocurable composition according to any one of <1> to <3>, wherein at least one di(meth)acrylic monomer constituting the (meth)acrylic monomer (X) is a compound represented by the following Formula (x-1):

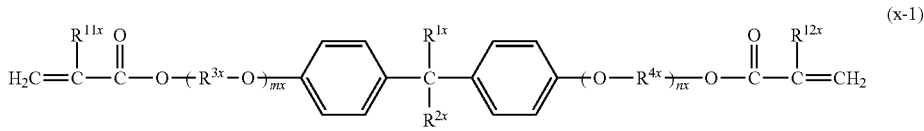

wherein, in Formula (x-1), each of $R^{1x}$, $R^{2x}$, $R^{11x}$, and $R^{12x}$ independently represents a hydrogen atom or a methyl group; each of $R^{3x}$ and $R^{4x}$ independently represents a straight chain or branched chain alkylene group having from 2 to 4 carbon atoms; and each of mx and nx independently represents a number from 0 to 4, and wherein mx and nx satisfy: $1 \leq (mx+nx) \leq 4$.

<5> The photocurable composition according to any one of <1> to <4>, wherein at least one di(meth)acrylic monomer constituting the (meth)acrylic monomer (X) is a compound represented by the following Formula (x-2):

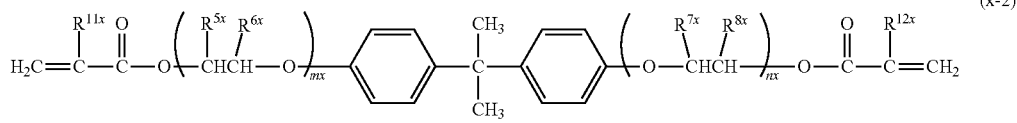

wherein, in Formula (x-2), each of $R^{5x}$, $R^{6x}$, $R^{7x}$, $R^{8x}$, $R^{11x}$, and $R^{12x}$ independently represents a hydrogen atom or a methyl group; and each of mx and nx independently represents a number from 0 to 4, and wherein mx and nx satisfy: $1 \leq (mx+nx) \leq 4$.

<6> The photocurable composition according to any one of <1> to <5>, wherein the (meth)acrylic monomer component further comprises at least one of:

a (meth)acrylic monomer (A) that is at least one selected from di(meth)acrylic monomers not containing, within one molecule, a hydroxyl group, a carboxy group, or an aromatic ring and containing, within one molecule, one or more ether bonds and two (meth)acryloyloxy groups, and that has a weight average molecular weight of from 200 to 400, a (meth)acrylic monomer (B) that is at least one selected from (meth)acrylic monomers not containing, within one molecule, a hydroxyl group, a carboxy group, or an aromatic ring and containing, within one molecule, a ring structure other than an aromatic ring and one (meth)acryloyloxy group, and that has a weight average molecular weight of from 130 to 240, a (meth)acrylic monomer (C) that is at least one selected from di(meth)acrylic monomers not containing, within one molecule, a hydroxyl group, a carboxy group, an ether bond, or an aromatic ring and containing, within one molecule, a hydrocarbon skeleton and two (meth)acryloyloxy groups, and that has a weight average molecular weight of from 190 to 280, or a (meth)acrylic monomer (D) that is at least one selected from (meth)acrylic monomers not containing, within one molecule, a hydroxyl group or a carboxy group and containing, within one molecule, an aromatic ring and one (meth)acryloyloxy group, and that has a weight average molecular weight of from 160 to 400.

<7> The photocurable composition according to <6>, wherein:

at least one di(meth)acrylic monomer constituting the (meth)acrylic monomer (A) is a compound represented by the following Formula (a-1);

at least one (meth)acrylic monomer constituting the (meth)acrylic monomer (B) is a compound represented by the following Formula (b-1);

at least one di(meth)acrylic monomer constituting the (meth)acrylic monomer (C) is a compound represented by the following Formula (c-1); and at least one (meth)acrylic monomer constituting the (meth)acrylic monomer (D) is a compound represented by the following Formula (d-1):

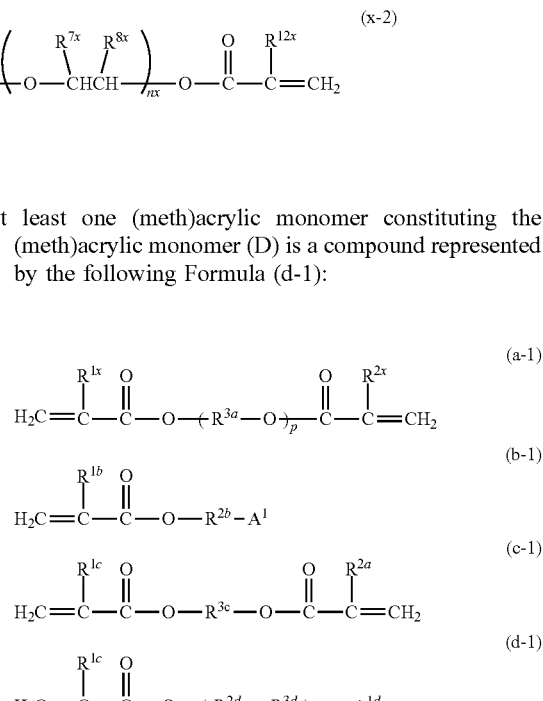

wherein, in Formula (a-1), each of $R^{1a}$ and $R^{2a}$ independently represents a hydrogen atom or a methyl group, each $R^{3a}$ independently represents a straight chain or branched chain alkylene group having from 2 to 4 carbon atoms; and p represents a number from 2 to 4;

in Formula (b-1), $R^{1b}$ represents a hydrogen atom or a methyl group; $R^{2b}$ represents a single bond or a methylene group; and $A^1$ represents a ring structure other than an aromatic ring;

in Formula (c-1), each of $R^{1c}$ and $R^{2c}$ independently represents a hydrogen atom or a methyl group; and $R^{3c}$ represents an alkylene group having from 1 to 9 carbon atoms; and in Formula (d-1), $R^{1d}$ represents a hydrogen atom or a methyl group; each $R^{2d}$ independently represents a straight chain or branched chain alkylene group having from 1 to 5 carbon atoms; each $R^{3d}$ independently represents a single bond, an ether bond (—O—), an ester bond (—O—(C═O)—), or —$C_6H_4$—O—; $A^{1d}$ represents an aromatic ring; and nd represents a number from 1 to 2.

<8> The photocurable composition according to <6> or <7>, wherein:
  at least one di(meth)acrylic monomer constituting the (meth)acrylic monomer (A) is a compound represented by the following Formula (a-2);
  at least one (meth)acrylic monomer constituting the (meth)acrylic monomer (B) is a compound represented by the following Formula (b-2);
  at least one di(meth)acrylic monomer constituting the (meth)acrylic monomer (C) is a compound represented by the following Formula (c-2); and
  at least one (meth)acrylic monomer constituting the (meth)acrylic monomer (D) is a compound represented by the following Formula (d-2):

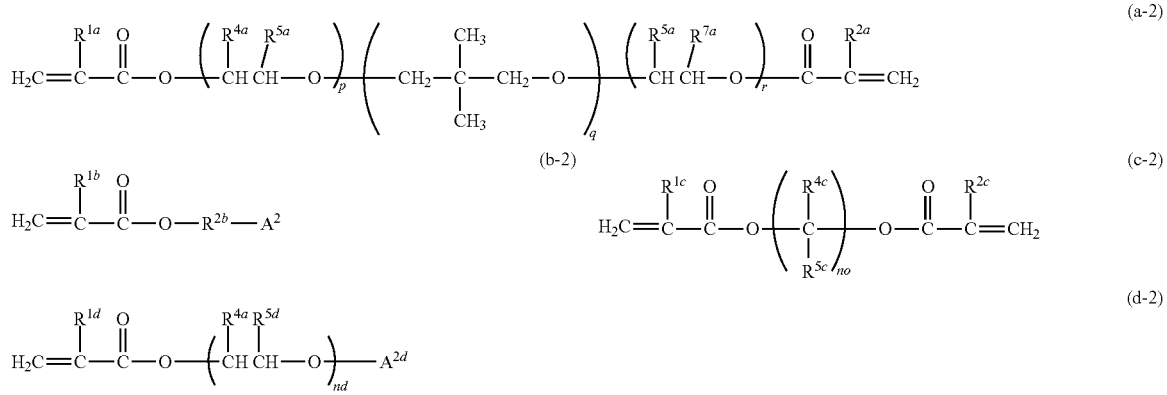

wherein,
in Formula (a-2), each of $R^{1a}$, $R^{2a}$, $R^{4a}$, $R^{5a}$, $R^{6a}$, and $R^{7a}$ independently represents a hydrogen atom or a methyl group; and each of p, q, and r independently represents 0 or 1, and wherein p, q, and r satisfy: p+q+r≥2;
in Formula (b-2), $R^{1b}$ represents a hydrogen atom or a methyl group; $R^{2b}$ represents a single bond or a methylene group; and $A^2$ represents a ring structure containing a dicyclopentenyl skeleton, a dicyclopentanyl skeleton, a cyclohexane skeleton, a tetrahydrofuran skeleton, a morpholine skeleton, an isobornyl skeleton, a norbornyl skeleton, a dioxolane skeleton, or a dioxane skeleton;
in Formula (c-2), each of $R^{1c}$ and $R^{2c}$ independently represents a hydrogen atom or a methyl group; each of $R^{4c}$ and $R^{5c}$ independently represents a hydrogen atom or a methyl group; and nc represents a number from 1 to 9, and wherein an alkylene group represented by —$(CR^{4c}R^{5c})_{nc}$— has from 1 to 9 carbon atoms; and
in Formula (d-2), each of $R^{1d}$, $R^{4d}$ and $R^{5d}$ independently represents a hydrogen atom or a methyl group; $A^{2d}$ represents an aromatic ring; and nd represents a number from 1 to 2.

<9> The photocurable composition according to any one of <1> to <8>, wherein a content of the acrylic monomer (X) is 100 parts by mass or more with respect to 1,000 parts by mass of a total content of the (meth)acrylic monomer component.

<10> The photocurable composition according to any one of <1> to <9>, wherein a content of the acrylic monomer (H) is from 60 parts by mass to 480 parts by mass with respect to 1,000 parts by mass of a total content of the (meth)acrylic monomer component.

<11> The photocurable composition according to any one of <6> to <8>, wherein a total content of the (meth)acrylic monomer (A), the (meth)acrylic monomer (B), the (meth) acrylic monomer (C) and the (meth)acrylic monomer (D) is from 30 parts by mass to 750 parts by mass with respect to 1,000 parts by mass of a total content of the (meth)acrylic monomer component.

<12> The photocurable composition according to any one of <1> to <11>, wherein the photopolymerization initiator is at least one selected from alkylphenone compounds or acylphosphine oxide compounds.

<13> The photocurable composition according to any one of <1> to <12>, wherein a content of the photopolymerization initiator is from 1 part by mass to 50 parts by mass with respect to 1,000 parts by mass of a total content of the (meth)acrylic monomer component.

<14> The photocurable composition according to any one of <1> to <13>, wherein the photocurable composition has a viscosity, as measured using a Type E viscometer at 25° C. and 50 rpm, of from 20 mPa·s to 1500 mPa·s.

<15> The photocurable composition according to any one of <1> to <14>, wherein the photocurable composition is used for production, by stereolithography, of a dental prosthesis, a medical device for intraoral use, or a tooth and jaw model.

<16> The photocurable composition according to any one of <1> to <14>, wherein the photocurable composition is used for production, by stereolithography, of a denture base or a mouthpiece.

<17> The photocurable composition according to any one of <1> to <14>, wherein the photocurable composition is used for production, by stereolithography, of a denture base.

<18> A denture base that is a cured product of the photocurable composition according to <17>.

<19> A plate denture comprising the denture base according to <18> and an artificial tooth fixed to the denture base.

Advantageous Effects of Invention

One embodiment of the invention provides a photocurable composition which is used in stereolithography, and which has an excellent flexural strength and flexural modulus as well as an excellent fracture toughness after being subjected to photocuring.

Further, one embodiment of the invention provides: a denture base which is a cured product of the above described photocurable composition and which has an excellent flexural strength and flexural modulus as well as an excellent fracture toughness; and a plate denture including the denture base.

DESCRIPTION OF EMBODIMENTS

In the present specification, any numerical range indicated using an expression "from * to" represents a range in which numerical values described before and after the "to" are included in the range as a lower limit value and an upper limit value.

Further, in the present specification, the term "ether bond" refers to a bond (a bond represented by —O—) in which two hydrocarbon groups are bound via an oxygen atom, as is commonly defined. Accordingly, "—O—" in an ester bond (—C(=O)—O—) is not included in the definition of the "ether bond".

In the present specification, the term "(meth)acrylic monomer" is a concept which encompasses both an acrylic monomer and a methacrylic monomer.

Further, in the present specification, the term "(meth) acrylate" is a concept which encompasses both acrylate and methacrylate.

Still further, in the present specification, the term "(meth) acryloyloxy group" is a concept which encompasses both acryloyloxy group and methacryloyloxy group.

[Photocurable Composition]

The photocurable composition according to one embodiment of the invention is a photocurable composition for use in stereolithography, wherein the photocurable composition includes:

a (meth)acrylic monomer component including:
  a (meth)acrylic monomer (X) that is at least one selected from di(meth)acrylic monomers not containing, within one molecule, a hydroxyl group or a carboxy group and containing, within one molecule, two aromatic rings and two (meth)acryloyloxy groups, and that has a weight average molecular weight of from 400 to 580, and
  a (meth)acrylic monomer (H) that is at least one selected from (meth)acrylic monomers containing, within one molecule, at least one of a hydroxyl group or a carboxy group, and a (meth)acryloyloxy group, and that has a weight average molecular weight of from 100 to 700; and
a photopolymerization initiator.

In this photocurable composition, the functional group value (a) as defined by the following Formula (a) is from $0.50 \times 10^{-3}$ mol/g to $2.00 \times 10^{-3}$ mol/g.

Functional group value $(a)=(n_H/M_H) \times P_H$      Formula (a)

[wherein, in Formula (a), $n_H$ represents the total number of hydroxyl groups and carboxy groups contained in one molecule of the (meth)acrylic monomer (H); $M_H$ represents the weight average molecular weight of the (meth)acrylic monomer (H); and $P_H$ represents the mass ratio of the (meth)acrylic monomer (H) with respect to the total amount of the (meth)acrylic monomer component].

The photocurable composition according to the present embodiment has an excellent flexural strength and flexural modulus as well as an excellent fracture toughness after being subjected to photocuring, due to containing a combination of the above described acrylic monomer (X) and the above described (meth)acrylic monomer (H), and due to the functional group value (a) being within the above described range.

Accordingly, a stereolithographed product, preferably, a dental prosthesis or the like (namely, a dental prosthesis, a medical device for intraoral use, or a tooth and jaw model; the same shall apply hereinafter; a denture base, in particular) which is produced by stereolithography, using the photocurable composition according to the present embodiment, also has an excellent flexural strength and flexural modulus as well as an excellent fracture toughness.

Further, the photocurable composition according to the present embodiment has a viscosity suitable for the production by stereolithography of a dental prosthesis or the like (a preferred embodiment of the stereolithographed product; the same shall apply hereinafter).

In the present specification, the "(meth)acrylic monomer component" refers to entire (meth)acrylic monomers included in the photocurable composition.

The "(meth)acrylic monomer component" includes at least the (meth)acrylic monomer (X) and the (meth)acrylic monomer (H).

The "(meth)acrylic monomer component" may include a (meth)acrylic monomer (A), a (meth)acrylic monomer (B), a (meth)acrylic monomer (C), a (meth)acrylic monomer (D) etc. to be described later.

In the photocurable composition according to the present embodiment, the flexural strength and flexural modulus after photocuring are improved due to the incorporation of the (meth)acrylic monomer (X), as compared to the case in which a (meth)acrylic monomer not containing, within one molecule, a hydroxyl group or a carboxy group and containing, within one molecule, one aromatic ring and one (meth)acryloyloxy group is included, instead of the (meth) acrylic monomer (X).

In the photocurable composition according to the present embodiment, the incorporation of the (meth)acrylic monomer (X) allows for inhibiting a phenomenon in which a crystallinity of the monomers is increased excessively, as compared to the case in which a di(meth)acrylic monomer not containing, within one molecule, a hydroxyl group or a carboxy group and containing, within one molecule, one aromatic ring and two (meth)acryloyloxy groups is included, instead of the (meth)acrylic monomer (X). As a result, the viscosity of the photocurable composition is reduced.

In the photocurable composition according to the present embodiment, the viscosity of the photocurable composition is reduced due to the incorporation of the (meth)acrylic monomer (X), as compared to the case in which a (meth) acrylic monomer not containing, within one molecule, a hydroxyl group or a carboxy group and containing, within one molecule, three or more aromatic rings is used, instead of the (meth)acrylic monomer (X).

In the photocurable composition according to the present embodiment, the fracture toughness after photocuring is improved due to the incorporation of the (meth)acrylic monomer (X), as compared to the case in which a (meth) acrylic monomer not containing, within one molecule, a hydroxyl group or a carboxy group and containing, within one molecule, three or more (meth)acryloyloxy groups is used, instead of the (meth)acrylic monomer (X).

The value 580, which is the upper limit of the weight average molecular weight of the (meth)acrylic monomer (X), is an upper limit value defined in terms of the flexural strength and the flexural modulus after photocuring.

The value 400, which is the lower limit of the weight average molecular weight of the (meth)acrylic monomer (X), is a lower limit value defined in terms of ease of production of the monomer or ease of availability.

Further, in the photocurable composition according to the present embodiment, the fracture toughness after photocuring is improved due to the incorporation of the (meth)acrylic monomer (H).

The reason for this is not clear; however it is thought to be due to generation of hydrogen bonds in the photocurable composition, as a result of the (meth)acrylic monomer (H) containing at least one of a hydroxyl group or a carboxy group. The thus generated hydrogen bonds are thought to cause an improvement in the fracture toughness after photocuring.

The value 700, which is the upper limit of the weight average molecular weight of the (meth)acrylic monomer (H), is an upper limit value defined in terms of the flexural strength and the flexural modulus after photocuring.

The value 100, which is the lower limit of the weight average molecular weight of the (meth)acrylic monomer (H), is a lower limit value defined in terms of the ease of production of the monomer or the ease of availability.

In addition, when the functional group value (a) of the photocurable composition according to the present embodiment is $0.50 \times 10^{-3}$ mol/g or more, the fracture toughness is improved.

When the functional group value (a) of the photocurable composition according to the present embodiment is $2.00 \times 10^{-3}$ mol/g or less, on the other hand, the flexural strength and the flexural modulus are improved.

As shown by the above described Formula (a), the functional group value (a) relates to the amount of hydroxyl groups and carboxy groups contained in the (meth)acrylic monomer component.

The functional group value (a) is from $0.50 \times 10^{-3}$ mol/g to $2.00 \times 10^{-3}$ mol/g, but preferably from $0.54 \times 10^{-3}$ mol/g to $1.94 \times 10^{-3}$ mol/g.

In the photocurable composition according to the present embodiment, it is preferable that the (meth)acrylic monomer component further includes at least one the following monomer, in terms of further improving the flexural strength and the flexural modulus:

- a (meth)acrylic monomer (A) that is at least one selected from di(meth)acrylic monomers not containing, within one molecule, a hydroxyl group, a carboxy group, or an aromatic ring and containing, within one molecule, one or more ether bonds and two (meth)acryloyloxy groups, and that has a weight average molecular weight of from 200 to 400,
- a (meth)acrylic monomer (B) that is at least one selected from (meth)acrylic monomers not containing, within one molecule, a hydroxyl group, a carboxy group, or an aromatic ring and containing, within one molecule, a ring structure other than an aromatic ring and one (meth)acryloyloxy group, and that has a weight average molecular weight of from 130 to 240,
- a (meth)acrylic monomer (C) that is at least one selected from di(meth)acrylic monomers not containing, within one molecule, a hydroxyl group, a carboxy group, an ether bond, or an aromatic ring and containing, within one molecule, a hydrocarbon skeleton and two (meth)acryloyloxy groups, and that has a weight average molecular weight of from 190 to 280, or
- a (meth)acrylic monomer (D) that is at least one selected from (meth)acrylic monomers not containing, within one molecule, a hydroxyl group or a carboxy group and containing, within one molecule, an aromatic ring and one (meth)acryloyloxy group, and that has a weight average molecular weight of from 160 to 400.

The photocurable composition according to the present embodiment preferably satisfies the following flexural strength and the following flexural modulus, after being subjected to photocuring, in terms of the practical use of the resulting dental prosthesis or the like (the resulting denture base, in particular).

In other words, the photocurable composition according to the present embodiment preferably satisfies a flexural strength, as measured below, of 60 MPa or more, and more preferably, 65 MPa or more. Specifically, the measurement of the flexural strength is carried out as follows. The photocurable composition is formed into a formed product having a size of 64 mm×10 mm×3.3 mm thickness, and the resulting formed product is subjected to UV light irradiation at 10 J/cm$^2$ to carry out photocuring, thereby obtaining a stereolithographed product (namely, a cured product; the same shall apply hereinafter). The resulting stereolithographed product is stored in a constant temperature water bath controlled at 37±1° C. for 50±2 hours, and the flexural strength of the stereolithographed product after storage is measured in accordance with ISO 20795-1: 2008 (or JIS T 6501: 2012).

Further, the photocurable composition according to the present embodiment preferably satisfies a flexural modulus, as measured below, of 1,500 MPa or more, and more preferably, 2,000 MPa or more. Specifically, the measurement of the flexural modulus is carried out as follows. The photocurable composition is formed into a formed product having a size of 64 mm×10 mm×3.3 mm thickness, and the resulting formed product is subjected to UV light irradiation at 10 J/cm$^2$ to carry out photocuring, thereby obtaining a stereolithographed product. The resulting stereolithographed product is stored in a constant temperature water bath controlled at 37±1° C. for 50±2 hours, and the flexural modulus of the stereolithographed product after storage is measured in accordance with ISO 20795-1: 2008 (or JIS T 6501: 2012).

In the present specification, the term "fracture toughness" refers to a total fracture work (J/cm$^2$) obtained by carrying out a fracture toughness test by a flexural test.

The photocurable composition according to the present embodiment preferably satisfies a total fracture work (J/m$^2$), as measured below, of 65 J/m$^2$ or more, and more preferably 70 J/m$^2$ or more, and still more preferably 75 J/m$^2$ or more. Specifically, the measurement of the total fracture work (J/m$^2$) is carried out as follows. The photocurable composition is formed into a formed product having a size of 39 mm×8 mm×thickness of 4 mm, and the resulting formed product is subjected to UV light irradiation at 10 J/cm$^2$ to carry out photocuring, thereby obtaining a stereolithographed product. The resulting stereolithographed product is stored in a constant temperature water bath controlled at 37±1° C. for 7 days ±2 hours, and the total fracture work (J/m$^2$) of the stereolithographed product after storage is measured by carrying out a fracture toughness test by a flexural test, in accordance with ISO 20795-1: 2008, at a push-in speed of 1.0±0.2 mm/min.

The photocurable composition according to the present embodiment is used for the production by stereolithography of a dental prosthesis or the like (namely, a dental prosthesis, a medical device for intraoral use, or a tooth and jaw model).

In the present embodiment, the dental prosthesis may be, for example, a denture base, a denture, an inlay, a crown, a bridge, a temporary crown, or a temporary bridge. Among these, a denture base is preferred.

Further, in the present embodiment, the medical device for intraoral use may be, for example, an orthodontic appliance (such as a mouthpiece, or an orthodontic appliance), a bite splint, a tray for obtaining an impression, or a guide for use in surgery. Among these, an orthodontic appliance is preferred, and a mouthpiece is more preferred.

The dental prosthesis or the like (namely, a dental prosthesis, a medical device for intraoral use, or a tooth and jaw model) is preferably a dental prosthesis or an orthodontic appliance, more preferably a denture base or a mouthpiece, and particularly preferably a denture base.

In the present embodiment, the term "stereolithography" refers to one of the three-dimensional shaping methods utilizing a 3D printer.

Examples of stereolithography methods include an SLA (Stereo Lithography Apparatus) method, a DLP (Digital Light Processing) method, and an ink-jet method.

The photocurable composition according to the present embodiment is particularly suitable for a SLA or a DLP stereolithography method.

Examples of the SLA method include a method in which a spot-shaped UV laser beam is irradiated to a photocurable composition to obtain a three-dimensional shaped product.

In a case in which a dental prosthesis or the like is produced by the SLA method, the production thereof may be carried out, for example, as follows. Specifically, the photocurable composition according to the present embodiment is pooled in a container, and a spot-like UV laser beam is selectively irradiated to a liquid surface of the photocurable composition so as to obtain a desired pattern. In this manner, the photocurable composition is cured to form a cured layer having a desired thickness on a shaping table. Subsequently, the shaping table is lowered, so that the photocurable composition in a liquid state is supplied over the cured layer, in an amount sufficient for forming one layer, and the curing is carried out in the same manner as described above. This operation is repeated to obtain cured layers disposed one on another in layers. In this manner, a dental prosthesis or the like can be produced.

Examples of the DLP method include a method in which planar light is irradiated to a photocurable composition to obtain a three-dimensional shaped product.

As to the method of obtaining a three-dimensional shaped product by the DLP method, the description in JP-B 5111880 and JP-B 5235056 can be referred to, if appropriate.

In a case in which a dental prosthesis or the like is produced by the DLP method, the production thereof may be carried out, for example, as follows. Specifically, a lamp which emits light other than a laser beam, such as a high pressure mercury lamp, an ultra-high pressure mercury lamp, or a low pressure mercury lamp, or alternatively, an LED is used as a light source. A planar drawing mask in which a plurality of digital micro mirror shutters are disposed planarly, is disposed between the light source and the surface of the photocurable composition to be shaped. Then light is irradiated to the surface of the photocurable composition to be shaped through the planar drawing mask, to form a cured layer having a predetermined pattern shape. This operation is repeated so that cured layers are formed and layered one on another, sequentially. In this manner, a dental prosthesis or the like can be produced.

Examples of the ink-jet method include a method in which droplets of a photocurable composition is continuously discharged onto a substrate through an ink-jet nozzle, and then light is irradiated to the droplets adhered to the substrate to obtain a three-dimensional shaped product.

In a case in which a dental prosthesis or the like is produced by an ink-jet method, the production thereof may be carried out, for example, as follows. Specifically, while scanning a plane with a head including an ink-jet nozzle and a light source, the photocurable composition is discharged onto a substrate through the ink-jet nozzle. At the same time, light is irradiated to the discharged photocurable composition to form a cured layer. This operation is repeated so that cured layers are formed and layered one on another, sequentially. In this manner, a dental prosthesis or the like can be produced.

The photocurable composition according to the present embodiment preferably has a viscosity at 25° C. and at 50 rpm, as measured using a Type E viscometer, of from 20 mPa·s to 1,500 mPa·s, in terms of suitability for the production by stereolithography of a dental prosthesis or the like. The lower limit of the viscosity is more preferably 50 mPa·s. The upper limit of the viscosity is more preferably 1,000 mPa·s, and still more preferably 500 mPa·s.

The viscosity at 25° C. and at 50 rpm of the photocurable composition according to the present embodiment may be adjusted depending on the method of the stereolithography to be used.

In a case in which a dental prosthesis or the like is produced by the SLA method, for example, the viscosity of the photocurable composition is preferably from 50 mPa·s to 1500 mPa·s, and more preferably from 50 mPa·s to 1000 mPa·s.

In a case in which a dental prosthesis or the like is produced by the DLP method, for example, the viscosity of the photocurable composition is preferably from 50 mPa·s to 500 mPa·s, and more preferably from 50 mPa·s to 250 mPa·s.

In a case in which a dental prosthesis or the like is produced by the ink-jet method, for example, the viscosity of the photocurable composition is preferably from 20 mPa·s to 500 mPa·s, and more preferably from 20 mPa·s to 100 mPa·s.

Components of the photocurable composition according to the present embodiment will now be described.

<(Meth)Acrylic Monomer (X)>

The (meth)acrylic monomer component included in the photocurable composition according to the present embodiment includes the (meth)acrylic monomer (X).

The (meth)acrylic monomer (X) is at least one selected from di(meth)acrylic monomers not containing, within one molecule, a hydroxyl group or a carboxy group and containing, within one molecule, two aromatic rings and two (meth)acryloyloxy groups, and has a weight average molecular weight of from 400 to 580.

In the photocurable composition according to the present embodiment, the (meth)acrylic monomer (X) mainly contributes to an improvement in the flexural strength and the flexural modulus after photocuring.

The above described (meth)acrylic monomer (X) may consist of one type of di(meth)acrylic monomer not containing, within one molecule, a hydroxyl group or a carboxy group and containing, within one molecule, two aromatic rings and two (meth)acryloyloxy groups, or may be a mixture composed of two or more types of the di(meth) acrylic monomers.

It is preferable that at least one the di(meth)acrylic monomer constituting the (meth)acrylic monomer (X) contains an ether bond within one molecule, in terms of further improving the fracture toughness after photocuring.

Specifically, when at least one the di(meth)acrylic monomer constituting the (meth)acrylic monomer (X) contains an ether bond within one molecule, the degree of freedom of molecular motion is increased to impart flexibility to the cured product after photocuring, thereby improving its toughness. As a result, the fracture toughness of the above described cured product (namely, the fracture toughness of the photocurable composition after photocuring) is improved.

is particularly preferable that mx+nx is from 2 to 3, in terms of further improving the flexural strength and the flexural modulus after photocuring.

It is still more preferable that at least one the di(meth) acrylic monomer constituting the (meth)acrylic monomer (X) is a compound represented by the following Formula (x-2), in terms of reducing the viscosity of the photocurable composition, and further improving the fracture toughness, the flexural strength, and the flexural modulus, after photocuring.

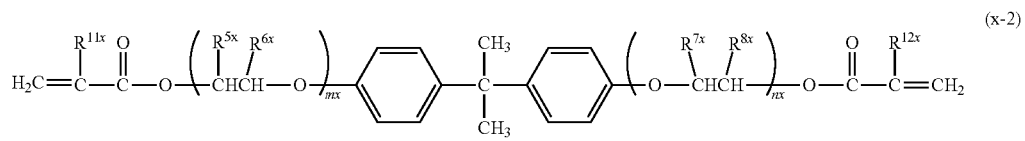

(x-2)

It is more preferable that at least one the di(meth)acrylic monomer contains from one to four ether bonds within one molecule.

When the number of ether bonds within one molecule, in at least one the di(meth)acrylic monomer, is four or less, the flexural strength and the flexural modulus after photocuring are further improved.

The number of ether bonds within one molecule is still more preferably from two to four, and particularly preferably from two to three, in terms of further improving the flexural strength and the flexural modulus after photocuring.

It is still more preferable that at least one the di(meth) acrylic monomer is a compound represented by the following Formula (x-1), in terms of reducing the viscosity of the photocurable composition, and further improving the fracture toughness, the flexural strength, and the flexural modulus, after photocuring.

In Formula (x-2), each of $R^{5x}$, $R^{6x}$, $R^{7x}$, $R^{8x}$, $R^{11x}$, and $R^{12x}$ independently represents a hydrogen atom or a methyl group; and each of mx and nx independently represents a number from 0 to 4, with the proviso that mx and nx satisfy: $1 \leq (mx+nx) \leq 4$.

In a case in which a plurality of $R^{5x}$s are present in the compound represented by Formula (x-2), the plurality of $R^{5x}$s may be the same as or different from each other. The same applies for each of $R^{6x}$, $R^{7x}$, and $R^{8x}$.

In Formula (x-2), it is preferable that one of $R^{5x}$ or $R^{6x}$ is a methyl group, and the other is a hydrogen atom. At the same time, it is preferable that one of $R^{7x}$ or $R^{8x}$ is a methyl group and the other is a hydrogen atom.

In Formula (x-2), it is particularly preferable that $R^{5x}$ and $R^{8x}$ are both methyl groups, and $R^{6x}$ and $R^{7x}$ are both hydrogen atoms.

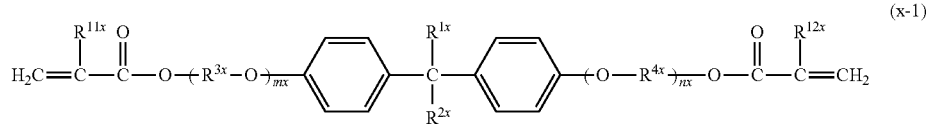

(x-1)

In Formula (x-1), each of $R^{1x}$, $R^{2x}$, $R^{11x}$, and $R^{12x}$ independently represents a hydrogen atom or a methyl group; each of $R^{3x}$ and $R^{4x}$ independently represents a straight chain or branched chain alkylene group having from 2 to 4 carbon atoms; and each of mx and nx independently represents a number from 0 to 4, with the proviso that mx and nx satisfy: $1 \leq (mx+nx) \leq 4$.

In a case in which a plurality of $R^{3x}$s are present in the compound represented by Formula (x-1), the plurality of $R^{3x}$s may be the same as or different from each other. The same applies for $R^{4x}$.

In Formula (x-1), each of $R^{1x}$ and $R^{2x}$ is preferably a methyl group.

Further, it is preferable that each of $R^{3x}$ and $R^{4x}$ independently represents an ethylene group, a trimethylene group, a tetramethylene group, a 1-methylethylene group, a 1-ethylethylene group or a 2-methyltrimethylene group, and more preferably, an ethylene group or a 1-methylethylene group.

In addition, it is preferable that both of $R^{3x}$ and $R^{4x}$ are ethylene groups, trimethylene groups, tetramethylene groups, 1-methylethylene groups, or 2-methyltrimethylene groups, and more preferably both are ethylene groups or 1-methylethylene groups. Although mx+nx is from 1 to 4, it Although mx+nx is from 1 to 4, it is particularly preferable that mx+nx is from 2 to 3, in terms of further improving the flexural strength and the flexural modulus after photocuring.

Specific examples of the (meth)acrylic monomer (X) include ethoxylated bisphenol A di(meth)acrylate (EO=2 mol, 2.2 mol, 2.6 mol, 3 mol, and 4 mol), propoxylated bisphenol A di(meth)acrylate (PO=2 mol, 3 mol, and 4 mol), and ethoxylated bisphenol F di(meth)acrylate (EO=2 mol, 2.2 mol, 2.6 mol, 3 mol, and 4 mol).

In the photocurable composition according to the present embodiment, the content of the (meth)acrylic monomer (X) is preferably 100 parts by mass or more, more preferably 300 parts by mass or more, still more preferably 400 parts by mass or more, still more preferably 500 parts by mass or more, and still more preferably 550 parts by mass or more, with respect to 1,000 parts by mass of the total content of the (meth)acrylic monomer component, in terms of reducing the viscosity of the composition, as well as improving the flexural strength and the flexural modulus after photocuring.

The content of the (meth)acrylic monomer (X) is not particularly limited as long as the content is less than 1,000 parts by mass, with respect to 1,000 parts by mass of the total content of the (meth)acrylic monomer component. However, in terms of the fracture toughness after photocuring, the content of the (meth)acrylic monomer (X) is preferably 950 parts by mass or less, more preferably 900 parts by mass or less, and still more preferably 800 parts by mass or less.

<(Meth)Acrylic Monomer (H)>

The (meth)acrylic monomer component included in the photocurable composition according to the present embodiment includes the (meth)acrylic monomer (H).

The (meth)acrylic monomer (H) is at least one selected from (meth)acrylic monomers containing, within one molecule, at least one of a hydroxyl group or a carboxy group, and a (meth)acryloyloxy group, and has a weight average molecular weight of from 100 to 700.

In the photocurable composition according to the present embodiment, the (meth)acrylic monomer (H) mainly contributes to an improvement in the fracture toughness after photocuring.

The above described (meth)acrylic monomer (H) may consist of one type of (meth)acrylic monomer containing, within one molecule, at least one of a hydroxyl group or a carboxy group, and a (meth)acryloyloxy group, or may be a mixture composed of two or more types of the (meth)acrylic monomers.

It is preferable that the (meth)acrylic monomer component included in the photocurable composition according to the present embodiment does not include, other than the (meth)acrylic monomer (H), any other (meth)acrylic monomer component containing, within one molecule, at least one of a hydroxyl group or a carboxy group.

The (meth)acrylic monomers constituting the (meth)acrylic monomer (H) may contain, within one molecule, only one functional group selected from a hydroxyl group or a carboxy group, or may contain two or more selected therefrom.

Further, the (meth)acrylic monomers constituting the (meth)acrylic monomer (H) may contain, within one molecule, only one (meth)acryloyloxy group, or may contain two or more selected therefrom.

Examples of the (meth)acrylic monomers constituting the (meth)acrylic monomer (H) include:

(meth)acrylic acid esters containing a hydroxyalkyl group having from 1 to 10 carbon atoms [such as 2-hydroxyethyl (meth)acrylate, 2-hydroxypropyl (meth)acrylate, 2-hydroxybutyl (meth)acrylate, 4-hydroxybutyl (meth)acrylate, 1,4-cyclohexanedimethanol mono(meth)acrylate, and the like];

(meth)acrylic acid adducts of diglycidyl ethers of aliphatic polyols having from 2 to 10 carbon atoms [such as (meth)acrylic acid adducts of ethylene glycol diglycidyl ethers, (meth)acrylic acid adducts of propylene glycol diglycidyl ethers, (meth)acrylic acid adducts of tripropylene glycol diglycidyl ethers, (meth)acrylic acid adducts of glycerin diglycidyl ethers, (meth)acrylic acid adducts of 1,6-hexanediol diglycidyl ethers, (meth)acrylic acid adducts of trimethylolpropane triglycidyl ethers, and the like];

(meth)acrylic acid adducts of phenyl glycidyl ethers;

(meth)acrylic acid adducts of diglycidyl ethers having a bisphenol skeleton [such as (meth)acrylic acid adducts of bisphenol A diglycidyl ethers, (meth)acrylic acid adducts of bisphenol F diglycidyl ethers, (meth)acrylic acid adducts of ethoxylated bisphenol A diglycidyl ethers, (meth)acrylic acid adducts of ethoxylated bisphenol F diglycidyl ethers, (meth)acrylic acid adducts of propoxylated bisphenol A diglycidyl ethers, (meth)acrylic acid adducts of propoxylated bisphenol F diglycidyl ethers, and the like];

(meth)acrylic acid adducts of diglycidyl ethers having a hydrogenated bisphenol skeleton [such as (meth)acrylic acid adducts of hydrogenated bisphenol A diglycidyl ethers, (meth)acrylic acid adducts of hydrogenated bisphenol F diglycidyl ethers, and the like];

(meth)acrylic acid esters of aliphatic polyols having from 2 to 10 carbon atoms [such as 2-hydroxy-3-acryloyloxypropyl (meth)acrylate, 2-hydroxy-3-methacryloyloxypropyl (meth)acrylate, pentaerythritol tri(meth)acrylate, glycerin di(meth)acrylate, and the like];

(meth)acrylic acid esters having a phthalate ester structure [2-(meth)acryloyloxyethyl-phthalic acid, 2-(meth)acryloyloxyethyl-2-hydroxyethyl-phthalic acid, and 2-(meth)acryloyloxyethyl-2-hydroxypropyl-phthalic acid];

(meth)acrylic acid esters having a hydrogenated phthalate ester structure [such as 2-(meth)acryloyloxyethyl-hexahydrophthalic acid, and the like];

benzophenones substituted by a substituent containing a (meth)acryloyloxy group, and by at least one of a hydroxyl group or a carboxy group [such as 2-hydroxy-4-(meth)acryloyloxybenzophenone, and the like]; and (meth)acrylic acid esters having a succinic acid monoester structure [such as 2-(meth)acryloyloxyethyl-succinic acid, and the like].

Specific examples of the (meth)acrylic monomers constituting the (meth)acrylic monomer (H) are shown below.

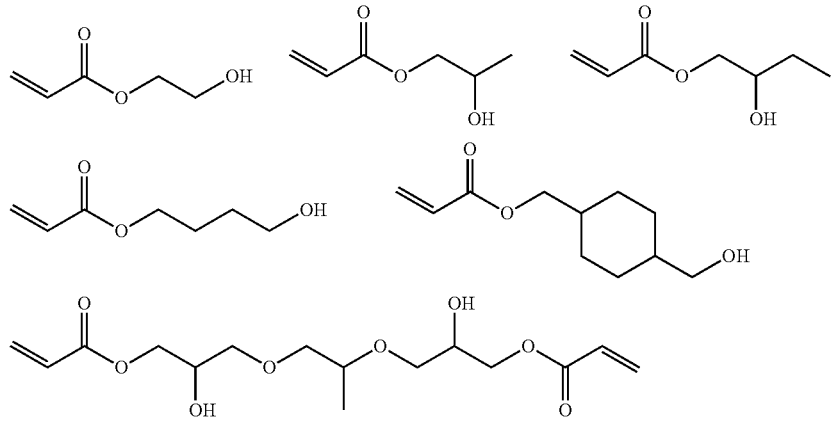

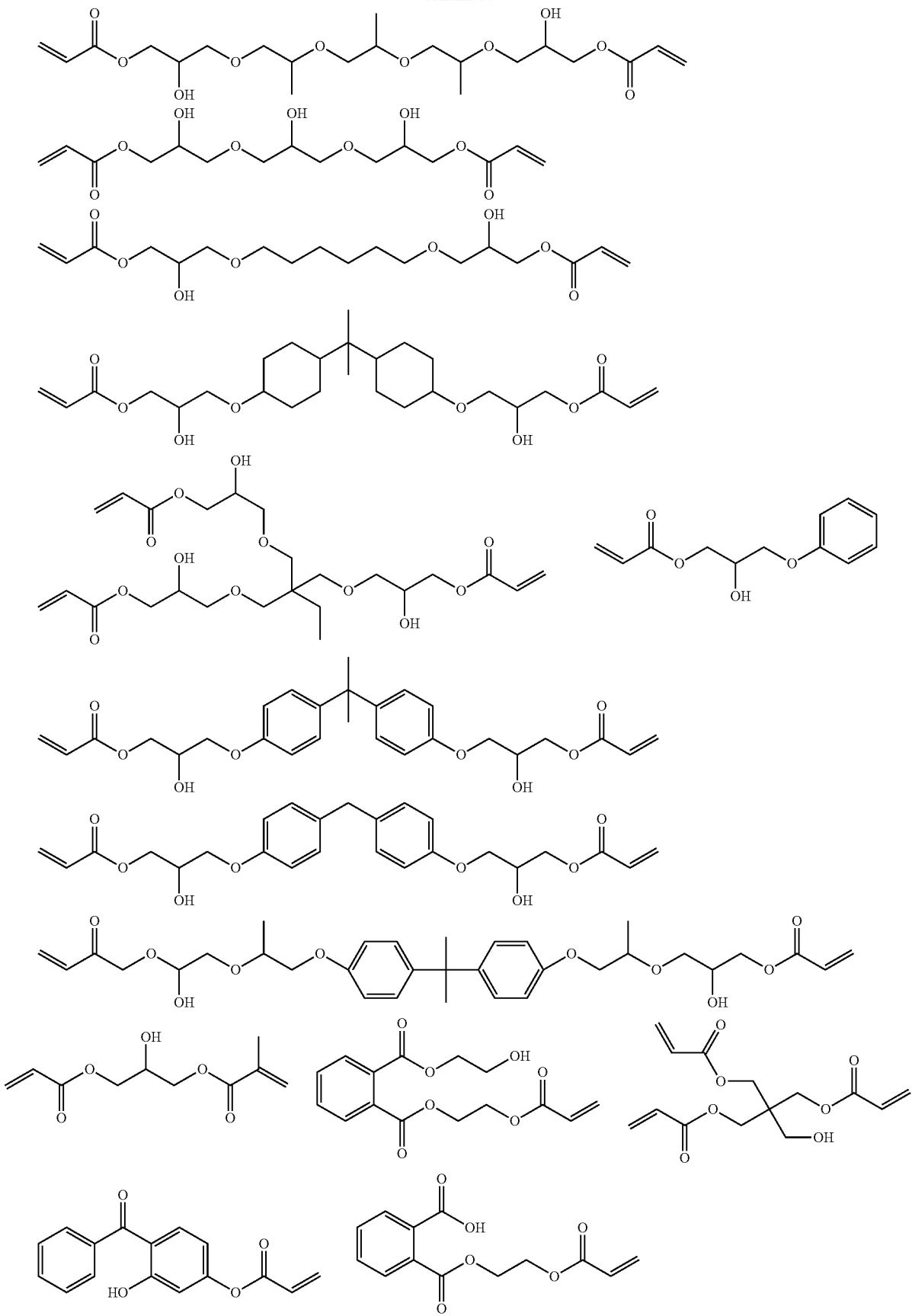

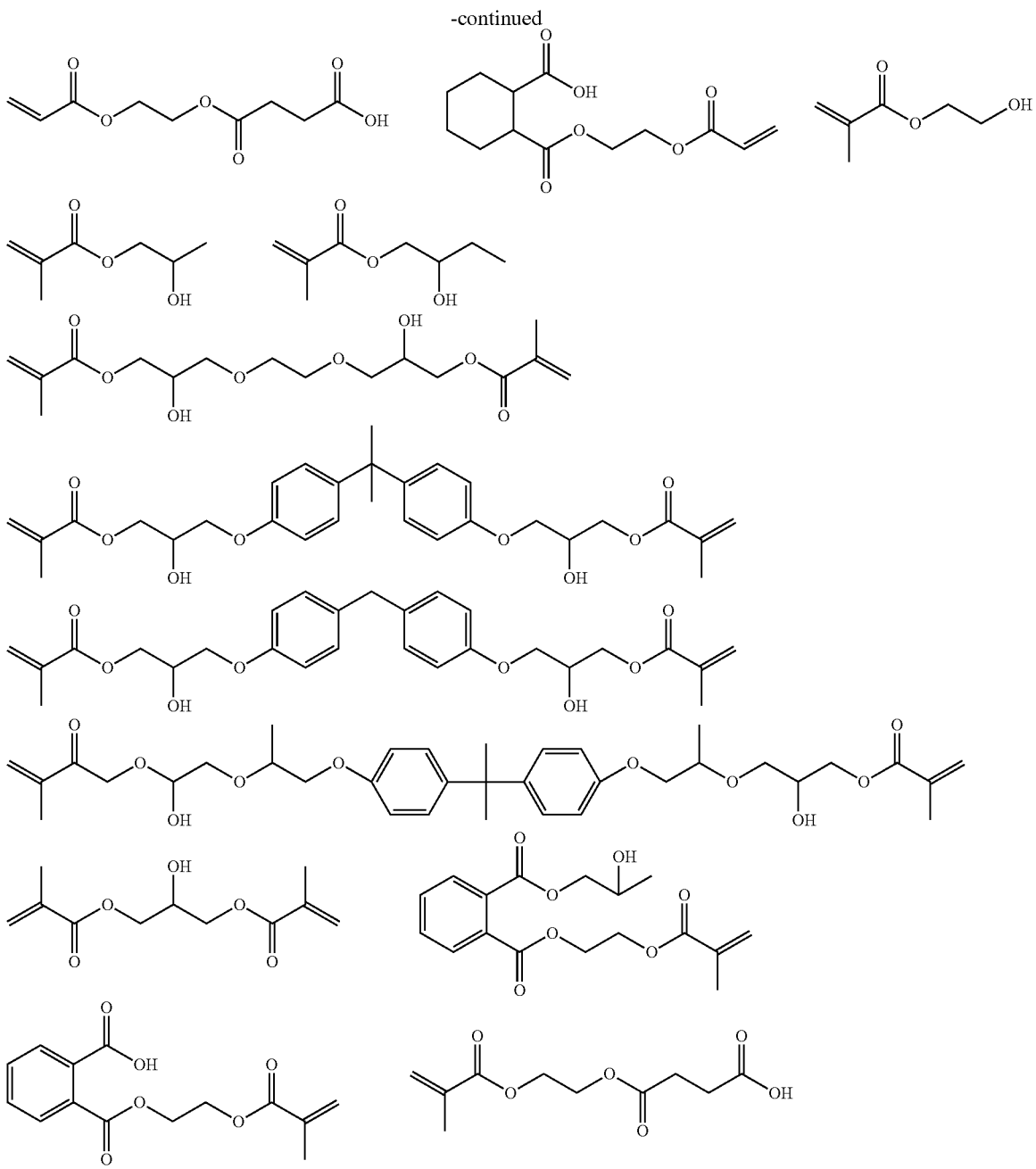

In the photocurable composition according to the present embodiment, the content of the (meth)acrylic monomer (H) is preferably from 60 parts by mass to 480 parts by mass, more preferably from 60 parts by mass to 400 parts by mass, and still more preferably from 80 parts by mass to 350 parts by mass, with respect to 1,000 parts by mass of the total content of the (meth)acrylic monomer component.

When the content of the (meth)acrylic monomer (H) is 60 parts by mass or more, the fracture toughness after photocuring is further improved.

When the content of the (meth)acrylic monomer (H) is 480 parts by mass or less, on the other hand, the flexural strength and the flexural modulus after photocuring is further improved.

The total content of the (meth)acrylic monomer (X) and the (meth)acrylic monomer (H) in the (meth)acrylic monomer component is preferably 30% by mass or more, more preferably 50% by mass or more, still more preferably 55% by mass or more, and still more preferably 60% by mass or more, with respect to the total amount of the (meth)acrylic monomer component. Further, the above described total content may be 100% by mass, or may be less than 100% by mass (for example, 95% by mass or less), with respect to the total amount of the (meth)acrylic monomer component.

<(Meth)Acrylic Monomer (A)>

The (meth)acrylic monomer component included in the photocurable composition according to the present embodiment may include the (meth)acrylic monomer (A) in some cases.

The (meth)acrylic monomer (A) is at least one selected from di(meth)acrylic monomers not containing, within one molecule, a hydroxyl group, a carboxy group, or an aromatic ring and containing, within one molecule, one or more ether bonds and two (meth)acryloyloxy groups, and has a weight average molecular weight of from 200 to 400.

In a case in which the (meth)acrylic monomer component includes the (meth)acrylic monomer (A), the flexural strength and the flexural modulus after photocuring is further improved.

The (meth)acrylic monomer (A) may consist of one type of di(meth)acrylic monomer not containing, within one molecule, a hydroxyl group, a carboxy group, or an aromatic ring and containing, within one molecule, one or more ether bonds and two (meth)acryloyloxy groups, or may be a mixture composed of two or more types of the di(meth)acrylic monomers.

It is preferable that at least one the di(meth)acrylic monomer constituting the (meth)acrylic monomer (A) contains one or two ether bonds within one molecule, in terms of further improving the fracture toughness after photocuring.

It is more preferable that at least one the di(meth)acrylic monomer constituting the (meth)acrylic monomer (A) is a compound represented by the following Formula (a-1), in terms of further improving the fracture toughness after photocuring.

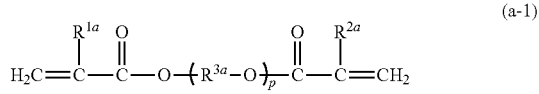

(a-1)

In Formula (a-1), each of $R^{1a}$ and $R^{2a}$ independently represents a hydrogen atom or a methyl group; each $R^{3a}$ independently represents a straight chain or branched chain alkylene group having from 2 to 4 carbon atoms; and p represents a number from 2 to 4.

In Formula (a-1), a plurality of $R^{3a}$s may be the same as or different from each other.

In Formula (a-1), p is preferably 2 or 3.

In Formula (a-1), it is preferable that $R^{1a}$ and $R^{2a}$ are both hydrogen atoms or are both methyl groups.

Further, it is preferable that each of $R^{3a}$s independently represents an ethylene group, a trimethylene group, a tetramethylene group, a 1-methylethylene group, a 1-ethylethylene group, a 2-methyltrimethylene group, or a 2,2-dimethyltrimethylene group, and more preferably an ethylene group, a 1-methylethylene group or a 2,2-dimethyltrimethylene group.

It is still more preferable that at least one the di(meth)acrylic monomer constituting the (meth)acrylic monomer (A) is a compound represented by the following Formula (a-2).

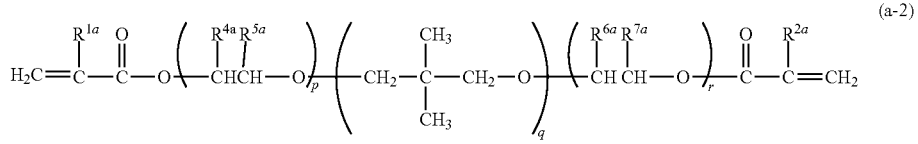

(a-2)

In Formula (a-2), each of $R^{1a}$, $R^{2a}$, $R^{4a}$, $R^{5a}$, $R^{6a}$, and $R^{7a}$ independently represents a hydrogen atom or a methyl group; and each of p, q, and r independently represents 0 or 1, with the proviso that p, q, and r satisfy: $p+q+r \geq 2$.

In Formula (a-2), it is preferable that $R^{1a}$ and $R^{2a}$ are both hydrogen atoms or both methyl groups. It is preferable that $R^{4a}$ and $R^{7a}$ are both hydrogen atoms or both methyl groups; and $R^{5a}$ and $R^{6a}$ are both hydrogen atoms or both methyl groups.

Further, it is preferable that p and r are both 1.

Although the (meth)acrylic monomer (A) has a weight average molecular weight of from 200 to 400, it is preferable that the (meth)acrylic monomer (A) has a weight average molecular weight of from 200 to 350, more preferably from 200 to 300, and particularly preferably from 200 to 250.

Examples of the (meth)acrylic monomer (A) include diethylene glycol di(meth)acrylate, triethylene glycol di(meth)acrylate, dipropylene glycol di(meth)acrylate, tripropylene glycol di(meth)acrylate, and propoxylated neopentyl glycol di(meth)acrylate.

<(Meth)Acrylic Monomer (B)>

The (meth)acrylic monomer component included in the photocurable composition according to the present embodiment may include the (meth)acrylic monomer (B) in some cases.

The (meth)acrylic monomer (B) is at least one selected from (meth)acrylic monomers not containing, within one molecule, a hydroxyl group, a carboxy group, or an aromatic ring and containing, within one molecule, a ring structure other than an aromatic ring and one (meth)acryloyloxy group, and has a weight average molecular weight of from 130 to 240.

In a case in which the (meth)acrylic monomer component includes the (meth)acrylic monomer (B), the flexural strength and the flexural modulus after photocuring is further improved.

The (meth)acrylic monomer (B) may consist of one type of (meth)acrylic monomer not containing, within one molecule, a hydroxyl group, a carboxy group, or an aromatic ring and containing, within one molecule, a ring structure other than an aromatic ring and one (meth)acryloyloxy group, or may be a mixture composed of two or more types of the (meth)acrylic monomers.

In the (meth)acrylic monomer (B), the ring structure other than an aromatic ring is preferably an alicyclic structure or a heterocyclic structure.

The ring structure other than an aromatic ring is more preferably a ring structure containing a dicyclopentenyl skeleton, a dicyclopentanyl skeleton, a cyclohexane skeleton, a tetrahydrofuran skeleton, a morpholine skeleton, an isobornyl skeleton, a norbornyl skeleton, a dioxolane skeleton, or a dioxane skeleton. The ring structure containing a skeleton as described above may contain a substituent such as an alkyl group (for example, a methyl group, an ethyl group, a propyl group, or a butyl group), or the like.

In the (meth)acrylic monomer (B), the ring structure other than an aromatic ring is preferably a polycyclic structure, and more preferably a ring structure containing a dicyclopentenyl skeleton, a dicyclopentanyl skeleton, an isobornyl skeleton, or a norbornyl skeleton, in terms of further improving the flexural strength and the flexural modulus after photocuring.

Further, at least one the (meth)acrylic monomer constituting the (meth)acrylic monomer (B) is preferably a compound which does not contain an imide structure, in terms of reducing water absorption.

It is still more preferable that at least one the (meth)acrylic monomer constituting the (meth)acrylic monomer (B) is a compound represented by the following Formula (b-1).

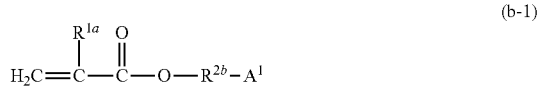

(b-1)

In Formula (b-1), $R^{1b}$ represents a hydrogen atom or a methyl group; $R^{2b}$ represents a single bond or a methylene group; and $A^1$ represents a ring structure other than an aromatic ring.

In Formula (b-1), preferred scope of the "ring structure other than an aromatic ring" represented by $A^1$ is as described above.

In other words, it is still more preferable that at least one the (meth)acrylic monomer constituting the (meth)acrylic monomer (B) is a compound represented by the following Formula (b-2).

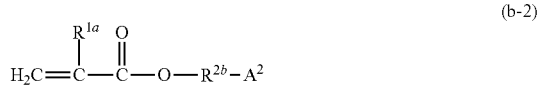

(b-2)

In Formula (b-2), $R^{1b}$ represents a hydrogen atom or a methyl group; $R^{2b}$ represents a single bond or a methylene group; and $A^2$ represents a ring structure containing a dicyclopentenyl skeleton, a dicyclopentanyl skeleton, a cyclohexane skeleton, a tetrahydrofuran skeleton, a morpholine skeleton, an isobornyl skeleton, a norbornyl skeleton, a dioxolane skeleton, or a dioxane skeleton.

The ring structure represented by $A^2$ may contain a substituent such as an alkyl group (for example, a methyl group, an ethyl group, a propyl group, or a butyl group), or the like.

Although the weight average molecular weight of the (meth)acrylic monomer (B) is from 130 to 240, it is preferable that the (meth)acrylic monomer (B) has a weight average molecular weight of from 150 or more 240 or less, and more preferably from 180 to 230.

Examples of the (meth)acrylic monomer (B) include isobornyl (meth)acrylate, norbornyl (meth)acrylate, dicyclopentenyl (meth)acrylate, dicyclopentanyl (meth)acrylate, cyclohexyl (meth)acrylate, tetrahydrofurfuryl (meth)acrylate, (meth)acryloylmorpholine, 4-tert-butylcyclohexanol (meth)acrylate, cyclohexanedimethanol di(meth)acrylate, (2-methyl-2-ethyl-1,3-dioxolane-4-yl) methyl acrylate, and cyclic trimethylolpropane formal acrylate.

<(Meth)Acrylic Monomer (C)>

The photocurable composition according to the present embodiment may include the (meth)acrylic monomer (C) in some cases.

The (meth)acrylic monomer (C) is at least one selected from di(meth)acrylic monomers not containing, within one molecule, a hydroxyl group, a carboxy group, an ether bond, or an aromatic ring and containing, within one molecule, a hydrocarbon skeleton and two (meth)acryloyloxy groups, and has a weight average molecular weight of from 190 to 280.

In a case in which the (meth)acrylic monomer component includes the (meth)acrylic monomer (C), the flexural strength and the flexural modulus after photocuring is further improved.

The (meth)acrylic monomer (C) may consist of one type of di(meth)acrylic monomer not containing, within one molecule, a hydroxyl group, a carboxy group, an ether bond, or an aromatic ring and containing, within one molecule, a hydrocarbon skeleton and two (meth)acryloyloxy groups, or may be a mixture composed of two or more types of the di(meth)acrylic monomers.

It is preferable that at least one the di(meth)acrylic monomer constituting the (meth)acrylic monomer (C) is a compound represented by the following Formula (c-1), in terms of further improving the flexural strength and the flexural modulus after photocuring.

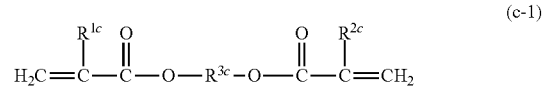

(c-1)

In Formula (c-1), each of $R^{1c}$ and $R^{2c}$ independently represents a hydrogen atom or a methyl group; and $R^3$ represents an alkylene group having from 1 to 9 carbon atoms.

The alkylene group represented by $R^{3c}$ may be a straight chain alkylene group, or a branched chain alkylene group.

Further, it is more preferable that at least one the di(meth)acrylic monomer constituting the (meth)acrylic monomer (C) is a compound represented by the following Formula (c-2), in terms of further improving the flexural strength and the flexural modulus after photocuring.

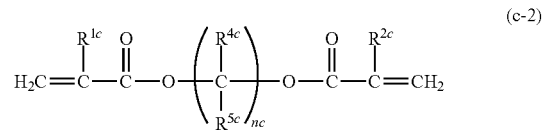

(c-2)

In Formula (c-2), each of $R^{1c}$ and $R^{2c}$ independently represents a hydrogen atom or a methyl group; each of $R^{4c}$ and $R^{5c}$ independently represents a hydrogen atom or a methyl group; and nc represents a number from 1 to 9, with the proviso that an alkylene group represented by $-(CR^{4c}R^{5c})_{nc}-$ has from 1 to 9 carbon atoms.

In a case in which a plurality of $R^{4c}$s are present in the compound represented by Formula (c-2), the plurality of $R^{4c}$s may be the same as or different from each other. The same applies for $R^{5c}$.

Specific examples of the (meth)acrylic monomer (C) include 1,3-butylene glycol diacrylate, neopentyl glycol diacrylate, 1,4-butanediol diacrylate, 1,4-butanediol dimethacrylate, 1,6-hexanediol diacrylate, 1,6-hexanediol dimethacrylate, 1,9-nonanediol diacrylate, ethylene glycol dimethacrylate, and 1,3-butylene glycol dimethacrylate.

<(Meth)Acrylic Monomer (D)>

The photocurable composition according to the present embodiment may include the (meth)acrylic monomer (D) in some cases.

The (meth)acrylic monomer (D) is at least one selected from (meth)acrylic monomers not containing, within one molecule, a hydroxyl group or a carboxy group and containing, within one molecule, an aromatic ring and one (meth)acryloyloxy group, and has a weight average molecular weight of from 160 to 400.

In a case in which the (meth)acrylic monomer component includes the (meth)acrylic monomer (D), the fracture toughness after photocuring is further improved.

The (meth)acrylic monomer (D) may consist of one type of (meth)acrylic monomer not containing, within one molecule, a hydroxyl group or a carboxy group and containing, within one molecule, an aromatic ring and one (meth)acryloyloxy group, or may be a mixture composed of two or more types of the (meth)acrylic monomers.

In the (meth)acrylic monomer (D), the aromatic ring is preferably a phenyl group or a naphthyl group, and more preferably a phenyl group. The aromatic ring may contain a substituent such as an alkyl group, an aryl group, an alkylaryl group, an aryloxy group, or the like. Further, the (meth)acrylic monomer (D) preferably contains one or two ether bonds or ester bonds (excluding those contained in the acryloyloxy group).

It is preferable that at least one the (meth)acrylic monomer constituting the (meth)acrylic monomer (D) is a compound represented by the following Formula (d-1), in terms of further improving the fracture toughness after photocuring.

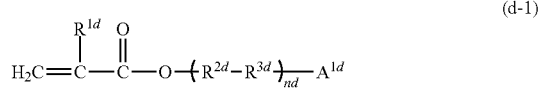
(d-1)

In Formula (d-1), $R^{1d}$ represents a hydrogen atom or a methyl group; each $R^{2d}$ independently represents a straight chain or branched chain alkylene group having from 1 to 5 carbon atoms; each $R^{3d}$ independently represents a single bond, an ether bond (—O—), an ester bond (—O—(C=O)—), or —$C_6H_4$—O—; $A^{1d}$ represents an aromatic ring; and nd represents a number from 1 to 2. The aromatic ring represented by $A^{1d}$ is preferably a phenyl group or a naphthyl group, and more preferably a phenyl group. Further, the aromatic ring may contain a substituent such as an alkyl group (for example, methyl group, ethyl group, propyl group, or butyl group), aryl group, alkylaryl group, aryloxy group, or the like. In addition, it is preferable that the compound represented by Formula (d-1) contains one or two ether bonds or ester bonds (excluding those contained in the acryloyloxy group).

Further, it is preferable that each $R^{2d}$ independently represents an ethylene group, a trimethylene group, a tetramethylene group, a pentamethylene group, a 1-methylethylene group, a 1-ethylethylene group, a 2-methyltrimethylene group, or a 2,2-dimethyltrimethylene group, and more preferably an ethylene group, a 1-methylethylene group or a 2,2-dimethyltrimethylene group.

It is more preferable that at least one the (meth)acrylic monomer constituting the (meth)acrylic monomer (D) is a compound represented by the following Formula (d-2), in terms of further improving the fracture toughness after photocuring.

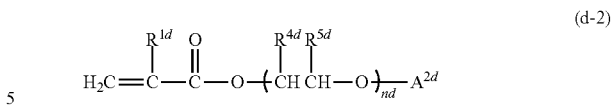
(d-2)

In Formula (d-2), each of $R^{1d}$, $R^{4d}$ and $R^{5d}$ independently represents a hydrogen atom or a methyl group; $A^{2d}$ represents an aromatic ring; and nd represents from 1 to 2. The aromatic ring represented by $A^{2d}$ is preferably a phenyl group or a naphthyl group, and more preferably a phenyl group. Further, the aromatic ring may contain a substituent such as an alkyl group (for example, methyl group, ethyl group, propyl group, or butyl group), aryl group, alkylaryl group, aryloxy group, or the like.

In a case in which a plurality of $R^{4d}$s are present in the compound represented by Formula (d-2), the plurality of $R^{4d}$s may be the same as or different from each other. The same applies for $R^{5d}$.

Although the weight average molecular weight of the (meth)acrylic monomer (D) is from 160 to 400, it is preferable that the (meth)acrylic monomer (D) has a weight average molecular weight of from 160 to 350, and more preferably from 180 to 300.

Specific examples of the (meth)acrylic monomer (D) include ethoxylated o-phenylphenol acrylate, ethoxylated o-phenylphenol EO-modified acrylate, ethoxylated p-cumylphenol acrylate, ethoxylated p-nonylphenol acrylate, ethoxylated p-methylphenol acrylate, neopentyl glycol-acrylic acid-benzoic acid ester, benzyl acrylate, m-phenoxybenzyl acrylate, and 2-(1-naphthoxy)ethyl acrylate.

In the photocurable composition according to the present embodiment, the total content of the (meth)acrylic monomer (A), the (meth)acrylic monomer (B), and the (meth)acrylic monomer (C) is preferably from 30 parts by mass to 750 parts by mass, and more preferably from 50 parts by mass to 700 parts by mass, with respect to 1,000 parts by mass of the total content of the (meth)acrylic monomer component.

Further, in the photocurable composition according to the present embodiment, the total content of the (meth)acrylic monomer (A), the (meth)acrylic monomer (B), the (meth)acrylic monomer (C), and the (meth)acrylic monomer (D) is preferably from 30 parts by mass to 750 parts by mass, and more preferably from 50 parts by mass to 700 parts by mass, with respect to 1,000 parts by mass of the total content of the (meth)acrylic monomer component.

The (meth)acrylic monomer component included in the photocurable composition according to the present embodiment may include at least one other (meth)acrylic monomer, other than the (meth)acrylic monomer (X), the (meth)acrylic monomer (H), the (meth)acrylic monomer (A), the (meth)acrylic monomer (B), the (meth)acrylic monomer (C), and the (meth)acrylic monomer (D) described above, to the extent that the effects of the invention are obtained.

Note, however, that the total content of the (meth)acrylic monomer (X), the (meth)acrylic monomer (H), the (meth)acrylic monomer (A), the (meth)acrylic monomer (B), and the (meth)acrylic monomer (C) in the (meth)acrylic monomer component is preferably 60% by mass or more, more preferably 80% by mass or more, and still more preferably 90% by mass or more, with respect to the total amount of the (meth)acrylic monomer component. The above described total content may be 100% by mass with respect to the total amount of the (meth)acrylic monomer component.

Further, the total content of the (meth)acrylic monomer (X), the (meth)acrylic monomer (H), the (meth)acrylic monomer (A), the (meth)acrylic monomer (B), the (meth) acrylic monomer (C), and the (meth)acrylic monomer (D) in the (meth)acrylic monomer component is preferably 60% by mass or more, more preferably 80% by mass or more, and still more preferably 90% by mass or more, with respect to the total amount of the (meth)acrylic monomer component. The above described total content may be 100% by mass with respect to the total amount of the (meth)acrylic monomer component.

<Photopolymerization Initiator>

The photocurable composition according to the present embodiment includes a photopolymerization initiator.

The photopolymerization initiator is not particularly limited as long as the photopolymerization initiator is capable of generating radicals when light is irradiated thereto. However, the photopolymerization initiator is preferably one which generates radicals by light irradiation at a wavelength used in the stereolithography.

In general, the wavelength of the light used in the stereolithography may be, for example, from 365 nm to 500 nm. However, the wavelength is preferably from 365 nm to 430 nm, and more preferably from 365 nm to 420 nm, in the view point of practical use.

Examples of the photopolymerization initiator which generates radicals by light irradiation at the wavelength used in the stereolithography include: alkylphenone compounds, acylphosphine oxide compounds, titanocene compounds, oxime ester compounds, benzoin compounds, acetophenone compounds, benzophenone compounds, thioxanthone compounds, α-acyloxime ester compounds, phenylglyoxylate compounds, benzyl compounds, azo compounds, diphenylsulfide compounds, organic pigment compounds, iron-phthalocyanine compounds, benzoin ether compounds, and anthraquinone compounds.

Among these, an alkylphenone compound and an acylphosphine oxide compound are preferred, in terms of reactivity and the like.

Examples of the alkylphenone compound include 1-hydroxy-cyclohexyl-phenyl-ketone (Irgacure 184: manufactured by BASF Japan Ltd.).

Examples of the acylphosphine oxide compound include bis(2,4,6-trimethylbenzoyl)-phenylphosphine oxide (Irgacure 819: manufactured by BASF Japan Ltd.), and 2,4,6-trimethylbenzoyl-diphenyl-phosphine oxide (Irgacure TPO: manufactured by BASF Japan Ltd.).

The photocurable composition according to the present embodiment may include only one type of the photopolymerization initiator, or two or more types of the photopolymerization initiators.

The content of the photopolymerization initiator (the total content, in a case in which two or more types thereof are included) in the photocurable composition according to the present embodiment is preferably from 1 part by mass to 50 parts by mass, more preferably from 2 parts by mass to 30 parts by mass, and still more preferably from 3 parts by mass to 25 parts by mass, with respect to 1,000 parts by mass of the total content of the (meth)acrylic monomer component.

<Other Components>

The photocurable composition according to the present embodiment may include at least one other component other than the (meth)acrylic monomer component and the photopolymerization initiator, if necessary.

Note, however, that the total content of the (meth)acrylic monomer component and the photopolymerization initiator is preferably from 60% by mass or more, more preferably from 80% by mass or more, and still more preferably from 90% by mass or more, with respect to the total amount of the photocurable composition.

Examples of the other components include coloring materials.

For example, in a case in which the photocurable composition according to the present embodiment is used for the production of a denture base, the photocurable composition may be colored to a color close to a gingival color by incorporating a coloring material, in terms of esthetics.

The coloring material is not limited as long as the coloring material does not interfere with the shaping of the photocurable composition by a 3D printer, and is less susceptible to discoloration. Examples thereof include pigments, dyes, and colorants. More specific examples of the coloring material include synthetic tar dyes, aluminum lakes of synthetic tar dyes, inorganic pigments, and natural pigments.

Further, examples of the other components also include other curable resins other than the above described (meth) acrylic monomer component (such as other curable monomers other than the above described (meth)acrylic monomer component).

In addition, examples of the other components also include thermal polymerization initiators.

In a case in which the photocurable composition according to the present embodiment includes a thermal polymerization initiator, it is possible to carry out both the photo-curing and heat curing in combination. Examples of the thermal polymerization initiator include thermal radical generators and amine compounds.

Still further, examples of the other components include: coupling agents such as silane coupling agents (for example, 3-acryloxypropyltrimethoxysilane); and additives such as rubber agents, ion-trapping agents, ion exchangers, leveling agents, plasticizers, and antifoaming agents.

The method of preparing the photocurable composition according to the present embodiment is not particularly limited. Examples thereof include a method in which the acrylic monomer (X), the (meth)acrylic monomer (C), and the photopolymerization initiator (and other component(s), if necessary) are mixed.

The means for mixing the respective components is not particularly limited. Examples thereof include: dissolution by ultrasonic wave; and mixing utilizing a twin arm mixer, a roll kneader, a twin-screw extruder, a ball mill kneader, or a planetary mixer.

The photocurable composition according to the present embodiment may be prepared by mixing the respective components, then filtering the resultant to remove impurities, and further subjecting the resultant to vacuum deaeration treatment.

[Photocured Product]

The method of carrying out photocuring using the photocurable composition according to the present embodiment is not particularly limited, and any of known methods and apparatuses can be used. For example, the photocuring may be carried out by a method in which a step of forming a thin film composed of the photocurable composition according to the present embodiment, and a step of obtaining a cured layer by irradiating light to the resulting thin film, are repeated a plurality of times, to dispose a plurality of cured layers one on another in layers, thereby obtaining a photocured product having a desired shape. The thus obtained photocured product may be used as it is, or may be used after being subjected to a post-curing by further light irradiation, heating or the like to improve its mechanical properties, morphological stability, and the like.

A glass transition temperature (Tg) after photocuring of the photocurable composition according to the present embodiment is not particularly limited. However, the glass transition temperature (Tg) after photocuring is preferably 70° C. or higher, and more preferably 80° C. or higher, in terms of the flexural strength and the flexural modulus.

At the same time, the glass transition temperature (Tg) after photocuring is preferably 140° C. or lower, in terms of the fracture toughness.

[Denture Base and Plate Denture]

The dental prosthesis or the like which is a cured product (namely, stereolithographed product) of the photocurable composition according to the present embodiment is particularly preferably a denture base. The denture base which is a cured product of the photocurable composition according to the present embodiment has an excellent flexural strength, flexural modulus and fracture toughness.

The denture base according to the present embodiment may be a denture base for use in a complete denture or a full denture, or alternatively, a denture base for use in a partial denture.

Further, the denture base according to the present embodiment may be a denture base for an upper jaw denture (hereinafter, also referred to as "upper jaw denture base"), or a denture base for a lower jaw denture (hereinafter, also referred to as "lower jaw denture base"), or alternatively, a set of an upper jaw denture base and a lower jaw denture base.

In addition, the denture base according to the present embodiment may be a denture base in which only a portion thereof is made of the photocurable composition according to the present embodiment, or a denture base entirely made of the photocurable composition according to the present embodiment.

Examples of the denture base in which only a portion thereof is made of the photocurable composition according to the present embodiment include: a denture base (a so-called metal base) which includes a metal portion and a resin portion, and in which at least one portion of the resin portion is made of the photocurable composition according to the present embodiment; and a denture base (a so-called resin base) which consists of a resin portion, and in which only a portion of the resin portion is made of the photocurable composition according to the present embodiment.

Examples of the denture base entirely made of the photocurable composition according to the present embodiment include a denture base consisting of a resin portion (a so-called resin base).

A plate denture according to the present embodiment includes the above described denture base according to the present embodiment and an artificial tooth fixed on the denture base.

Thus, the denture base included in the plate denture according to the present embodiment has an excellent flexural strength, flexural modulus and fracture toughness The plate denture according to the present embodiment may be a partial denture or a complete denture. In other words, the number of the artificial teeth to be included in the plate denture according to the present embodiment is not particularly limited, as long as the plate denture includes one artificial tooth.

Further, the plate denture according to the present embodiment may be an upper jaw denture, or a lower jaw denture, or alternatively, a set of an upper jaw denture and a lower jaw denture.

Examples of materials for the artificial tooth include an acrylic resin. Further, the artificial tooth may contain a filler and/or the like, in addition to the acrylic resin.

EXAMPLES

The present invention is now described more specifically, with reference to Examples. However, the invention is in no way limited to these Examples.

Examples 1 to 51 and Comparative Examples 1 to 10

<Preparation of Photocurable Compositions>

The components shown in the following Tables 1 to 6 were mixed to obtain photocurable compositions of Examples and Comparative Examples.

The functional group values (a) shown in Tables 1 to 6 were each calculated according to the above described Formula (a).

As an example, the calculated result of the functional group value (a) in Example 1 is shown below.

$$\text{Functional group value } (a) \text{ in Example } 1 = (n_H/M_H) \times P_H = (1/144) \times (80/1000) = 0.56 \times 10^{-3} \text{ (mol/g)}$$

The functional group values (a) in other Examples and Comparative Examples were calculated in the same manner as described above.

<Measurements and Evaluations>

The following measurements and evaluations were performed, using each of the resulting photocurable compositions. The results are shown in Tables 1 to 6.

(Viscosity of Photocurable Compositions)

The viscosity of each of the photocurable compositions was measured by a Type E viscometer, under conditions of 25° C. and 50 rpm.

(Flexural Strength and Flexural Modulus of Stereolithographed Products)

Each of the resulting photocurable compositions was formed into a size of 64 mm×10 mm×3.3 mm thickness using a 3D printer (MASTER PLUS S 2011; manufactured by Carima Co., Ltd.), to obtain a formed product. The resulting formed product was subjected to irradiation of UV light having a wavelength of 365 nm, at 10 J/cm², to carry out main curing, thereby obtaining a stereolithographed product.

The resulting stereolithographed product (hereinafter, referred to as "test specimen") was stored in a constant temperature water bath maintained at 37±1° C. for 50±2 hours.

Then, the test specimen was retrieved from the constant temperature water bath, and the flexural strength and the flexural modulus of the retrieved test specimen were each measured in accordance with ISO 20795-1: 2008. These measurements were carried out using a tensile test apparatus (manufactured by INTESCO Co., Ltd.), at a speed of 5±1 mm/min.

In a case in which each of the above obtained photocurable compositions is used in the production of a dental prosthesis or the like (a denture base, in particular), each stereolithographed product preferably has a flexural strength of 60 MPa or more, and more preferably 65 MPa.

Further, in this case, each photocurable composition preferably has a flexural modulus of 1,500 MPa or more, and more preferably 2.000 MPa or more.

(Total Fracture Work Measured by Fracture Toughness Test by Flexural Test)

Each of the resulting photocurable compositions was formed into a size of 39 mm×8 mm×4 mm thickness using a 3D printer (MASTER PLUS S2011; manufactured by Carima Co., Ltd.), to obtain a formed product. The resulting formed product was subjected to irradiation of UV light having a wavelength of 365 nm, at 10 J/cm$^2$, to carry out main curing of the formed product, thereby obtaining a stereolithographed product.

The resulting stereolithographed product (hereinafter, referred to as "test specimen") was stored in a constant temperature water bath maintained at 37±1° C. for 7 days ±2 hours.

Then, the test specimen was retrieved from the constant temperature water bath, and the retrieved test specimen was subjected to a fracture toughness test by a flexural test in accordance with ISO 20795-1: 2008, to measure the total fracture work (J/m$^2$) thereof. The fracture toughness test by a flexural test (measurement of the total fracture work) was carried out using a tensile test apparatus (manufactured by INTESCO Co., Ltd.), at a push-in speed of 1.0±0.2 mm/min.

In the above described measurement, a higher numerical value of the total fracture work indicates a higher fracture toughness.

In a case in which each of the above obtained photocurable compositions is used in the production of a dental prosthesis or the like (a denture base, in particular), the total fracture work of each stereolithographed product is preferably 65 J/m$^2$ or more, more preferably 70 J/m$^2$ or more, and particularly preferably 75 J/m$^2$ or more.

TABLE 1

| | | | Type | Mw | Example 1 | Example 2 | Example 3 | Example 4 | Example 5 | Example 6 | Example 7 | Example 8 | Example 9 | Example 10 | Example 11 |
|---|---|---|---|---|---|---|---|---|---|---|---|---|---|---|---|
| Photocurable composition | (Meth)acrylic monomer (X) | | A-BPE-2 | 424 | 620 | 600 | 640 | | | | | | | 620 | 630 |
| | | | ABE-300 | 469 | | | | 680 | 700 | 670 | 520 | 620 | 460 | | |
| | | | A-BPE-4 | 513 | | | | | | | | | | | |
| | | | A-BPP-3 | 511 | | | | | | | | | | | |
| | | | M-208 | 485 | | | | | | | | | | | |
| | | | BP-2EM | 479 | | | | | | | | | | | |
| | (Meth)acrylic monomer (A) (B) or (C) | (C) | NP-A | 212 | 300 | 200 | 80 | 240 | 100 | 220 | 200 | 260 | 190 | | |
| | | (A) | APG-100 | 242 | | | | | | | | | | 300 | 170 |
| | | (B) | IBXA | 208 | | | | | | | | | | | |
| | | (A) | 2EG | 242 | | | | | | | | | | | |
| | (Meth)acrylic monomer (H) | OH | 4HBA | 144 | 80 | 200 | 280 | 80 | 200 | | | | | 80 | 200 |
| | | OH | CHD-MMA | 198 | | | | | | 110 | 280 | | | | |
| | | OH | M-600A | 222 | | | | | | | | 120 | 350 | | |
| | | OH | HOA-MPE | 308 | | | | | | | | | | | |
| | | OH | 3000A | 485 | | | | | | | | | | | |
| | | OH | 70PA | 332 | | | | | | | | | | | |
| | | COOH | HOA-MPL | 264 | | | | | | | | | | | |
| | | COOH | HOA-MS | 216 | | | | | | | | | | | |
| | | OH | HPMA | 144 | | | | | | | | | | | |
| | | OH | 3000-MK | 513 | | | | | | | | | | | |
| | | OH | 40EM | 346 | | | | | | | | | | | |
| | Photopolymerization initiator | | Ir819 Ir184 TPO | | 10 | 10 | 10 | 10 | 10 | 10 | 10 | 10 | 10 | 10 | 10 |
| | Functional group value (a) (×10$^{-3}$ mol/g) | | | | 0.56 | 1.39 | 1.94 | 0.56 | 1.39 | 0.56 | 1.41 | 0.54 | 1.58 | 0.56 | 1.39 |
| Evaluation | Viscosity (mPa·s) | | | | 150 | 135 | 150 | 160 | 135 | 170 | 160 | 160 | 160 | 210 | 190 |
| | Flexural strength (MPa) | | | | 73 | 69 | 66 | 67 | 66 | 71 | 68 | 71 | 67 | 81 | 75 |
| | Flexural modulus (MPa) | | | | 2290 | 2080 | 2020 | 2120 | 2035 | 2315 | 2140 | 2260 | 2080 | 2510 | 2300 |
| | Total fracture work (J/m$^2$) | | | | 78 | 100 | 110 | 107 | 116 | 98 | 113 | 106 | 131 | 87 | 109 |

TABLE 2

| | | Type | Mw | Example 12 | Example 13 | Example 14 | Example 15 | Example 16 | Example 17 | Example 18 | Example 19 | Example 20 | Example 21 | Example 22 |
|---|---|---|---|---|---|---|---|---|---|---|---|---|---|---|
| Photocurable composition | (Meth)acrylic monomer (X) | A-BPE-2 | 424 | 640 | | | | | | | 650 | 670 | 690 | 630 |
| | | ABE-300 | 469 | | 620 | 620 | 600 | 620 | 580 | 500 | | | | |
| | | A-BPL-4 | 513 | | | | | | | | | | | |
| | | A-BPP-3 | 511 | | | | | | | | | | | |
| | | M-208 | 485 | | | | | | | | | | | |
| | | BP-2EM | 479 | | | | | | | | | | | |
| | (Meth)acrylic monomer (A) (B) or (C) | (C) NP-A | 212 | | | | | | | | | | | |
| | | (A) APG-100 | 242 | 80 | 280 | 180 | 270 | 180 | 290 | 250 | | | | |
| | | (B) IBM | 208 | | | | | | | | 270 | 130 | 30 | 240 |
| | | (A) 2EG | 242 | | | | | | | | | | | |
| | (Meth)acrylic monomer (H) | OH 4HBA | 144 | 280 | 100 | 200 | | | | | 80 | 200 | 280 | |
| | | OH CHD-MMA | 198 | | | | 130 | 200 | | | | | | 130 |
| | | OH M-600A | 222 | | | | | | 130 | 250 | | | | |
| | | OH HOA-MPE | 308 | | | | | | | | | | | |
| | | OH 3000A | 485 | | | | | | | | | | | |
| | | OH 70PA | 332 | | | | | | | | | | | |
| | | COOH HOA-MPL | 264 | | | | | | | | | | | |
| | | COOH HOA-MS | 216 | | | | | | | | | | | |
| | | OH HPMA | 144 | | | | | | | | | | | |
| | | OH 3000-MK | 513 | | | | | | | | | | | |
| | | OH 40EM | 346 | | | | | | | | | | | |
| | Photopolymerization initiator | Ir819 Ir184 TPO | | 10 | 10 | 10 | 10 | 10 | 10 | 10 | 10 | 10 | 10 | 10 |
| | | Functional group value (a) (×10⁻³ mol/g) | | 1.94 | 0.69 | 1.39 | 0.66 | 1.01 | 0.59 | 1.13 | 0.56 | 1.39 | 1.94 | 0.66 |
| Evaluation | | Viscosity (mPa·s) | | 220 | 140 | 130 | 140 | 130 | 155 | 150 | 145 | 170 | 180 | 170 |
| | | Flexural strength (MPa) | | 69 | 72 | 67 | 70 | 66 | 73 | 66 | 83 | 79 | 70 | 81 |
| | | Flexural modulus (MPa) | | 2030 | 2205 | 2065 | 2315 | 2190 | 2310 | 2170 | 2550 | 2420 | 2140 | 2530 |
| | | Total fracture work (J/m²) | | 128 | 102 | 117 | 114 | 136 | 104 | 130 | 86 | 92 | 104 | 92 |

TABLE 3

| | | Type | Mw | Example 23 | Example 24 | Example 25 | Example 26 | Example 27 | Example 28 | Example 29 | Example 30 | Example 31 | Example 32 | Example 33 |
|---|---|---|---|---|---|---|---|---|---|---|---|---|---|---|
| Photocurable composition | (Meth)acrylic monomer (X) | A-BPE-2 | 424 | 600 | 520 | 420 | | | | | | | | |
| | | ABE-300 | 469 | | | | 750 | 700 | 600 | 500 | 100 | 630 | 640 | 640 |
| | | A-BRE-4 | 513 | | | | | | | | | | | |
| | | A-BPP-3 | 511 | | | | | | | | | | | |
| | | M-208 | 485 | | | | | | | | | | | |
| | | BP-2EM | 479 | | | | | | | | | | | |
| | (Meth)acrylic monomer (A) (B) or (C) | (C) NP-A | 212 | | | | | | | | 250 | 650 | 170 | 160 | 160 |
| | | (A) APG-100 | 242 | | | | | | | | | | | |
| | | (B) IBXA | 208 | 200 | 350 | 280 | | | | | | | | |
| | | (A) 2EG | 242 | | | | 50 | 100 | 200 | | | | | |
| | (Meth)acrylic monomer (H) | OH 4HBA | 144 | | | | 200 | | | | | | | |
| | | OH CHC-MMA | 198 | 200 | | | | 200 | | | | | | |
| | | OH M-600A | 222 | | 130 | 300 | | | 200 | | | | | |

TABLE 3-continued

|  |  | Type | Mw | Example 23 | Example 24 | Example 25 | Example 26 | Example 27 | Example 28 | Example 29 | Example 30 | Example 31 | Example 32 | Example 33 |
|---|---|---|---|---|---|---|---|---|---|---|---|---|---|---|
|  | OH | HOA-MPE | 308 |  |  |  |  |  |  | 250 |  |  |  |  |
|  | OH | 3000A | 485 |  |  |  |  |  |  |  | 250 |  |  |  |
|  | OH | 70PA | 332 |  |  |  |  |  |  |  |  | 200 |  |  |
|  | COOH | HOA-MPL | 264 |  |  |  |  |  |  |  |  |  | 200 |  |
|  | COOH | HOA-MS | 216 |  |  |  |  |  |  |  |  |  |  | 200 |
|  | OH | HPMA | 144 |  |  |  |  |  |  |  |  |  |  |  |
|  | OH | 3000-MK | 513 |  |  |  |  |  |  |  |  |  |  |  |
|  | OH | 40EM | 346 |  |  |  |  |  |  |  |  |  |  |  |
| Photopolymerization initiator |  | Ir819 Ir184 TPO |  | 10 | 10 | 10 | 10 | 10 | 10 | 10 | 10 | 10 | 10 | 10 |
| Functional group value (a) (×10⁻³ mol/g) |  |  |  | 1.01 | 0.59 | 1.35 | 1.39 | 1.01 | 0.90 | 0.81 | 1.03 | 1.20 | 0.76 | 0.93 |
| Evaluation | Viscosity (mPa·s) |  |  | 155 | 135 | 170 | 190 | 185 | 170 | 220 | 240 | 180 | 170 | 160 |
|  | Flexural strength (MPa) |  |  | 78 | 82 | 74 | 67 | 68 | 72 | 68 | 67 | 68 | 70 | 69 |
|  | Flexural modulus (MPa) |  |  | 2475 | 2510 | 2185 | 2060 | 2090 | 2290 | 2175 | 2105 | 2090 | 2235 | 2190 |
|  | Total fracture work (J/m²) |  |  | 97 | 113 | 124 | 129 | 125 | 128 | 104 | 114 | 121 | 117 | 113 |

TABLE 4

|  |  |  | Type | Mw | Example 34 | Example 35 | Example 36 | Example 37 | Example 38 | Example 39 | Example 40 | Example 41 | Example 42 | Example 43 |
|---|---|---|---|---|---|---|---|---|---|---|---|---|---|---|
| Photocurable composition | (Meth)acrylic monomer (X) |  | A-BPE-2 | 424 |  |  |  | 600 |  |  |  |  |  |  |
|  |  |  | ABE-300 | 469 | 670 | 100 | 630 |  | 620 | 460 |  |  |  |  |
|  |  |  | A-BRE-4 | 513 |  |  |  |  |  |  | 700 |  |  |  |
|  |  |  | A-BPR3 | 511 |  |  |  |  |  |  |  | 630 |  |  |
|  |  |  | M-208 | 485 |  |  |  |  |  |  |  |  | 400 |  |
|  |  |  | BP-2EM | 479 |  |  |  |  |  |  |  |  |  | 700 |
|  | (Meth)acrylic monomer (A) (B) or (C) | (C) | NP-A | 212 | 130 | 680 | 170 | 200 |  | 190 | 150 | 220 | 450 | 150 |
|  |  | (A) | APG-100 | 242 |  |  |  |  | 180 |  |  |  |  |  |
|  |  | (B) | IBXA | 208 |  |  |  |  |  |  |  |  |  |  |
|  |  | (A) | 2E-G | 242 |  |  |  |  |  |  |  |  |  |  |
|  | (Meth)acrylic monomer (H) | OH | 4HBA | 144 |  |  |  | 200 | 200 |  | 150 | 150 | 150 | 150 |
|  |  | OH | CHDMMA | 198 |  |  |  |  |  |  |  |  |  |  |
|  |  | OH | M-600 | 222 |  |  |  |  |  | 350 |  |  |  |  |
|  |  | OH | HOA-MPE | 308 |  |  |  |  |  |  |  |  |  |  |
|  |  | OH | 3000A | 485 |  |  |  |  |  |  |  |  |  |  |
|  |  | OH | 70PA | 332 |  |  |  |  |  |  |  |  |  |  |
|  |  | COOH | HOA-MPL | 264 |  |  |  |  |  |  |  |  |  |  |
|  |  | COOH | HOA-MS | 216 |  |  |  |  |  |  |  |  |  |  |
|  |  | OH | HPMA | 144 | 200 |  |  |  |  |  |  |  |  |  |
|  |  | OH | 3000MK | 513 |  | 220 |  |  |  |  |  |  |  |  |
|  |  | OH | 40EM | 346 |  |  | 200 |  |  |  |  |  |  |  |
|  | Photopolymerization initiator |  | Ir819 |  | 10 | 10 | 10 |  |  |  | 10 | 10 | 10 | 10 |
|  |  |  | Ir184 |  |  |  |  | 10 | 10 | 10 |  |  |  |  |
|  |  |  | TPO |  |  |  |  | 10 | 10 | 10 |  |  |  |  |
|  | Functional group value (a) (×10⁻³ mol/g) |  |  |  | 1.39 | 0.86 | 1.16 | 1.39 | 1.39 | 1.58 | 1.04 | 1.04 | 1.04 | 1.04 |
| Evaluation | Viscosity (mPa·s) |  |  |  | 135 | 260 | 160 | 130 | 125 | 155 | 175 | 180 | 120 | 105 |
|  | Flexural strength (MPa) |  |  |  | 68 | 71 | 69 | 68 | 66 | 68 | 66 | 66 | 67 | 80 |
|  | Flexural modulus (MPa) |  |  |  | 2105 | 2195 | 2115 | 2070 | 2060 | 2090 | 2050 | 2020 | 2090 | 2485 |
|  | Total fracture work (J/m²) |  |  |  | 108 | 102 | 108 | 105 | 119 | 129 | 132 | 114 | 124 | 113 |

TABLE 5

|  |  |  | Type | Mw | Comparative Example 1 | Comparative Example 2 | Comparative Example 3 | Comparative Example 4 | Comparative Example 5 |
|---|---|---|---|---|---|---|---|---|---|
| Photocurable composition | (Meth)acrylic monomer (X) |  | A-BPE-2 | 424 | 660 | 650 | 670 |  |  |
|  |  |  | ABE-300 | 469 |  |  |  | 660 |  |
|  |  |  | A-BPE-4 | 513 |  |  |  |  | 680 |
|  |  |  | A-BPP-3 | 511 |  |  |  |  |  |
|  |  |  | M-208 | 485 |  |  |  |  |  |
|  |  |  | BP-2EM | 479 |  |  |  |  |  |
|  | (Meth)acrylic monomer (A) (B) or (C) | (C) | NP-A | 212 | 340 | 310 |  | 340 | 320 |
|  |  | (A) | APG-100 | 242 |  |  |  |  |  |
|  |  | (B) | IBXA | 208 |  |  |  |  |  |
|  |  | (A) | 2EG | 242 |  |  |  |  |  |
|  | (Meth)acrylic monomer (H) | OH | 4HBA | 144 |  | 40 | 330 |  |  |
|  |  | OH | CHDMMA | 198 |  |  |  |  |  |
|  |  | OH | M-600A | 222 |  |  |  |  |  |
|  |  | OH | HOA-MPE | 308 |  |  |  |  |  |
|  |  | OH | 3000A | 485 |  |  |  |  |  |
|  |  | OH | 70PA | 332 |  |  |  |  |  |
|  |  | COOH | HOA-MPL | 264 |  |  |  |  |  |
|  |  | COOH | HOA-MS | 216 |  |  |  |  |  |
|  |  | OH | HPMA | 144 |  |  |  |  |  |
|  |  | OH | 3000MK | 513 |  |  |  |  |  |
|  |  | OH | 40EM | 346 |  |  |  |  |  |
|  | Photopolymerization initiator |  | Ir819 |  | 10 | 10 | 10 | 10 | 10 |
|  |  |  | Ir184 |  |  |  |  |  |  |
|  |  |  | TPO |  |  |  |  |  |  |
|  | Functional group value (a) (×10$^{-3}$ mol/g) |  |  |  | 0.00 | 0.28 | 2.29 | 0.00 | 0.00 |
| Evaluation | Viscosity (mPa · s) |  |  |  | 160 | 155 | 130 | 160 | 160 |
|  | Flexural strength (MPa) |  |  |  | 79 | 78 | 57 | 75 | 66 |
|  | Flexural modulus (MPa) |  |  |  | 2390 | 2370 | 1840 | 2270 | 2030 |
|  | Total fracture work (J/m$^2$) |  |  |  | 43 | 51 | 130 | 50 | 47 |

|  |  |  | Type | Mw | Comparative Example 6 | Comparative Example 7 | Comparative Example 8 | Comparative Example 9 | Comparative Example 10 |
|---|---|---|---|---|---|---|---|---|---|
| Photocurable composition | (Meth)acrylic monomer (X) |  | A-BPE-2 | 424 |  |  |  |  |  |
|  |  |  | ABE-300 | 469 |  | 670 | 480 | 660 | 350 |
|  |  |  | A-BPE-4 | 513 |  |  |  |  |  |
|  |  |  | A-BPP-3 | 511 |  |  |  |  |  |
|  |  |  | M-208 | 485 |  |  |  |  |  |
|  |  |  | BP-2EM | 479 | 700 |  |  |  |  |
|  | (Meth)acrylic monomer (A) (B) or (C) | (C) | NP-A | 212 | 300 | 280 | 20 | 290 | 150 |
|  |  | (A) | APG-100 | 242 |  |  |  |  |  |
|  |  | (B) | IBXA | 208 |  |  |  |  |  |
|  |  | (A) | 2EG | 242 |  |  |  |  |  |
|  | (Meth)acrylic monomer (H) | OH | 4HBA | 144 |  |  |  |  |  |
|  |  | OH | CHDMMA | 198 |  | 50 | 500 |  |  |
|  |  | OH | M-600A | 222 |  |  |  | 50 | 500 |
|  |  | OH | HOA-MPE | 308 |  |  |  |  |  |
|  |  | OH | 3000A | 485 |  |  |  |  |  |
|  |  | OH | 70PA | 332 |  |  |  |  |  |
|  |  | COOH | HOA-MPL | 264 |  |  |  |  |  |
|  |  | COOH | HOA-MS | 216 |  |  |  |  |  |
|  |  | OH | HPMA | 144 |  |  |  |  |  |
|  |  | OH | 3000MK | 513 |  |  |  |  |  |
|  |  | OH | 40EM | 346 |  |  |  |  |  |
|  | Photopolymerization initiator |  | Ir819 |  | 10 | 10 | 10 | 10 | 10 |
|  |  |  | Ir184 |  |  |  |  |  |  |
|  |  |  | TPO |  |  |  |  |  |  |
|  | Functional group value (a) (×10$^{-3}$ mol/g) |  |  |  | 0.00 | 0.25 | 2.53 | 0.23 | 2.25 |
| Evaluation | Viscosity (mPa · s) |  |  |  | 120 | 150 | 165 | 160 | 170 |
|  | Flexural strength (MPa) |  |  |  | 87 | 73 | 54 | 76 | 48 |
|  | Flexural modulus (MPa) |  |  |  | 2680 | 2330 | 1840 | 2310 | 1590 |
|  | Total fracture work (J/m$^2$) |  |  |  | 32 | 58 | 184 | 56 | 287 |

TABLE 6

| | | Type | Mw | Example 44 | Example 45 | Example 46 | Example 47 | Example 48 | Example 49 | Example 50 | Example 51 |
|---|---|---|---|---|---|---|---|---|---|---|---|
| Photocurable composition | (Meth)acrylic monomer (X) | A-BPE-2 | 424 | | | | | | | | |
| | | ABE-300 | 469 | | | 650 | | | 650 | | |
| | | A-BPE-4 | 513 | 650 | 650 | | 650 | 650 | | 550 | 550 |
| | | A-BPP-3 | 511 | | | | | | | | |
| | | M-208 | 485 | | | | | | | | |
| | | BP-2EM | 479 | | | | | | | | |
| | (Meth)acrylic monomer (A) (B) or (C) | (C) NP-A | 212 | | | | | | | | |
| | | (A) APG-100 | 242 | | | | | | | | |
| | | (B) IBXA | 208 | | | | | | | | |
| | | (A) 2EG | 242 | | | | | | | | |
| | | (D) A-LEN-10 | 268 | 200 | | | 200 | | | 150 | 150 |
| | | (D) PO-A | 192 | | 200 | | | 200 | | | |
| | | (D) AMP-20GY | 236 | | | 200 | | | 200 | | |
| | (Meth)acrylic monomer (H) | OH 4HBA | 144 | 150 | 150 | 150 | | | | | |
| | | OH CHDMMA | 198 | | | | | | | | |
| | | OH M-600A | 222 | | | | 150 | 150 | 150 | 300 | 300 |
| | | OH HOA-MPE | 308 | | | | | | | | |
| | | OH 3000A | 485 | | | | | | | | |
| | | OH 70PA | 332 | | | | | | | | |
| | | COOH HOA-MPL | 264 | | | | | | | | |
| | | COOH HOA-MS | 216 | | | | | | | | |
| | | OH HPMA | 144 | | | | | | | | |
| | | OH 3000MK | 513 | | | | | | | | |
| | | OH 40EM | 346 | | | | | | | | |
| | Photopolymerization initiator | Ir819 | | 10 | 10 | 10 | 10 | 10 | 10 | 10 | |
| | | Ir184 | | | | | | | | | 10 |
| | | TPO | | | | | | | | | 10 |
| | Functional group value (a) (×10$^{-3}$ mol/g) | | | 1.04 | 1.04 | 1.04 | 0.67 | 067 | 0.67 | 1.35 | 1.35 |
| Evaluation | Viscosity (mPa·s) | | | 180 | 125 | 170 | 355 | 290 | 310 | 340 | 350 |
| | Flexural strength (MPa) | | | 68 | 67 | 68 | 77 | 74 | 72 | 72 | 71 |
| | Flexural modulus (MPa) | | | 2105 | 2050 | 2065 | 2320 | 2290 | 2225 | 2210 | 2190 |
| | Total fracture work (J/m$^2$) | | | 142 | 152 | 144 | 149 | 152 | 157 | 162 | 156 |

In Tables 1 to 6, each of the numbers shown in the fields of "Composition of the photocurable composition" in the respective Examples and Comparative Examples is indicated in "parts by mass".

The respective structures of (meth)acrylic monomers (X) listed in Tables 1 to 6 are as shown below.

In Tables 1 to 6. A-BPE-2, ABE-300, A-BPE-4, and A-BPP-3 are acrylic monomers manufactured by Shin-Nakamura Chemical Co., Ltd.: M-208 is an acrylic monomer manufactured by TOAGOSEI CO., LTD.; and BP-2EM is a methacrylic monomer manufactured by Kyoeisha Chemical Co., Ltd.

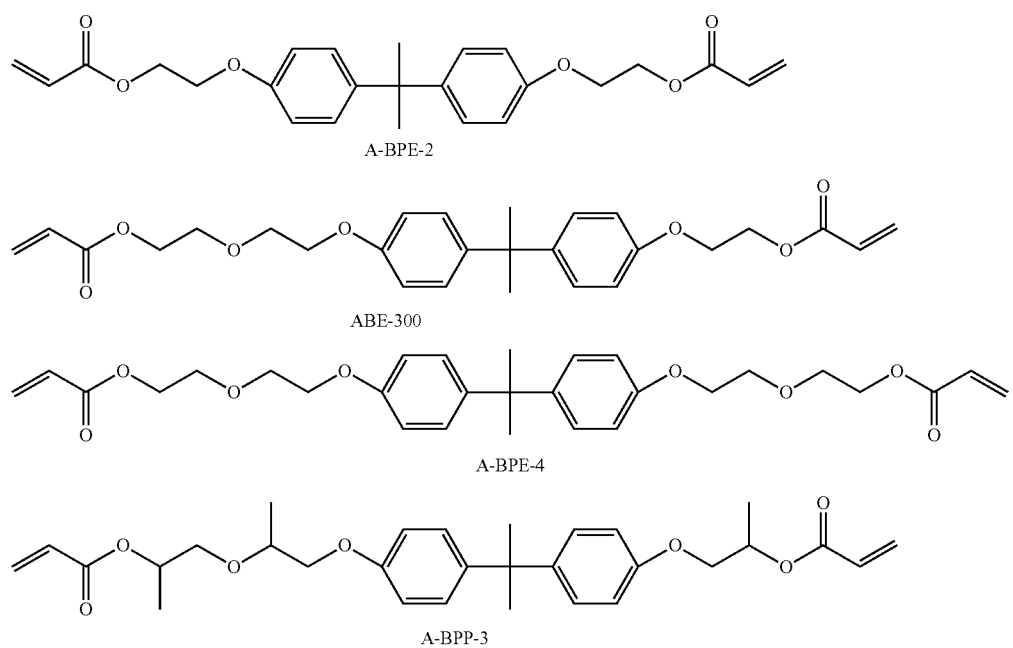

A-BPE-2

ABE-300

A-BPE-4

A-BPP-3

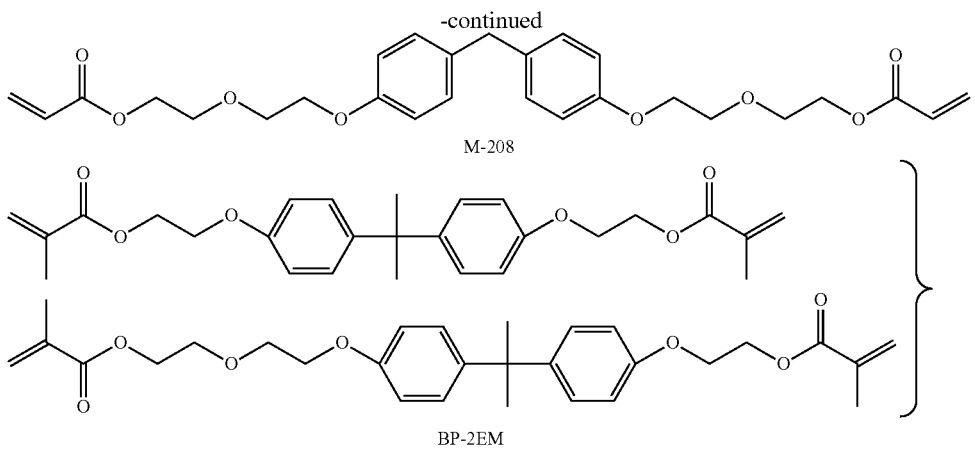

M-208

BP-2EM

In Tables 1 to 6, NP-A, which is the (meth)acrylic monomer (C), is an acrylic monomer manufactured by Kyoeisha Chemical Co., Ltd., and the structure thereof is as shown below.

APG-100, which is the (meth)acrylic monomer (A), is an acrylic monomer manufactured by Shin Nakamura Chemical Co., Ltd., and the structure thereof is as shown below.

IBXA, which is the (meth)acrylic monomer (B), is an acrylic monomer manufactured by Kyoeisha Chemical Co., Ltd., and the structure thereof is as shown below.

2EG, which is the (meth)acrylic monomer (A), is a methacrylic monomer manufactured by Kyoeisha Chemical Co., Ltd., and the structure thereof is as shown below.

A-LEN-10, which is the (meth)acrylic monomer (D), is an acrylic monomer manufactured by Shin Nakamura Chemical Co., Ltd., and the structure thereof is as shown below.

PO-A, which is the (meth)acrylic monomer (D), is an acrylic monomer manufactured by Kyoeisha Chemical Co., Ltd., and the structure thereof is as shown below.

Further, AMP-20GY, which is the (meth)acrylic monomer (D), is an acrylic monomer manufactured by Shin Nakamura Chemical Co., Ltd., and the structure thereof is as shown below.

NP-A

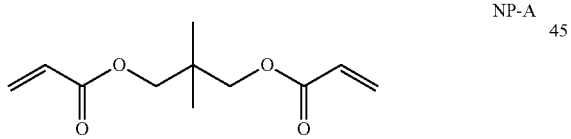

APG-100

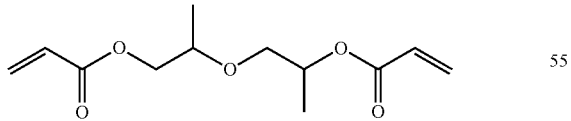

IB-XA

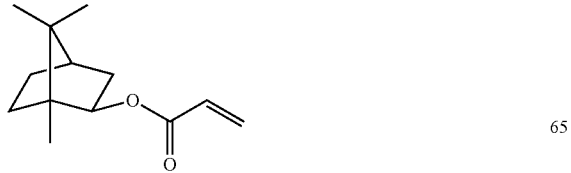

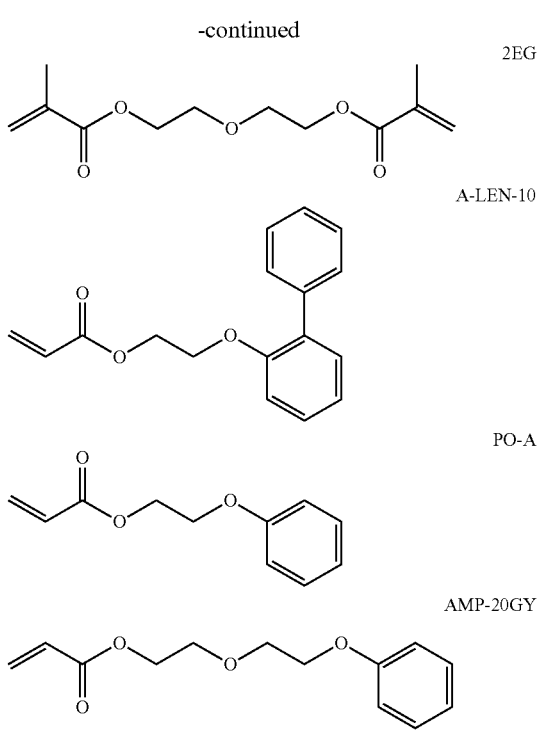

2EG

A-LEN-10

PO-A

AMP-20GY

In the fields of the (meth)acrylic monomer (H), in Tables 1 to 6, the description "OH" indicates that the (meth)acrylic monomer (H) is a (meth)acrylic monomer containing a hydroxyl group, and the description "COOH" indicates that the (meth)acrylic monomer (H) is a (meth)acrylic monomer containing a carboxy group.

The respective structures of (meth)acrylic monomers (H) listed in Tables 1 to 6 are as shown below.

In Tables 1 to 6,

4HBA is an acrylic monomer manufactured by Osaka Organic Chemical Industry Ltd.; CHDMMA is an acrylic monomer manufactured by Nippon Kasei Chemical Co., Ltd.; each of M-600A, HOA-MPE, 3000A, 70PA, HOA-MPL, and HOA-MS is an acrylic monomer manufactured by Kyoeisha Chemical Co., Ltd.; and each of HPMA, 3000MK, and 40EM, is a methacrylic monomer manufactured by Kyoeisha Chemical Co., Ltd.

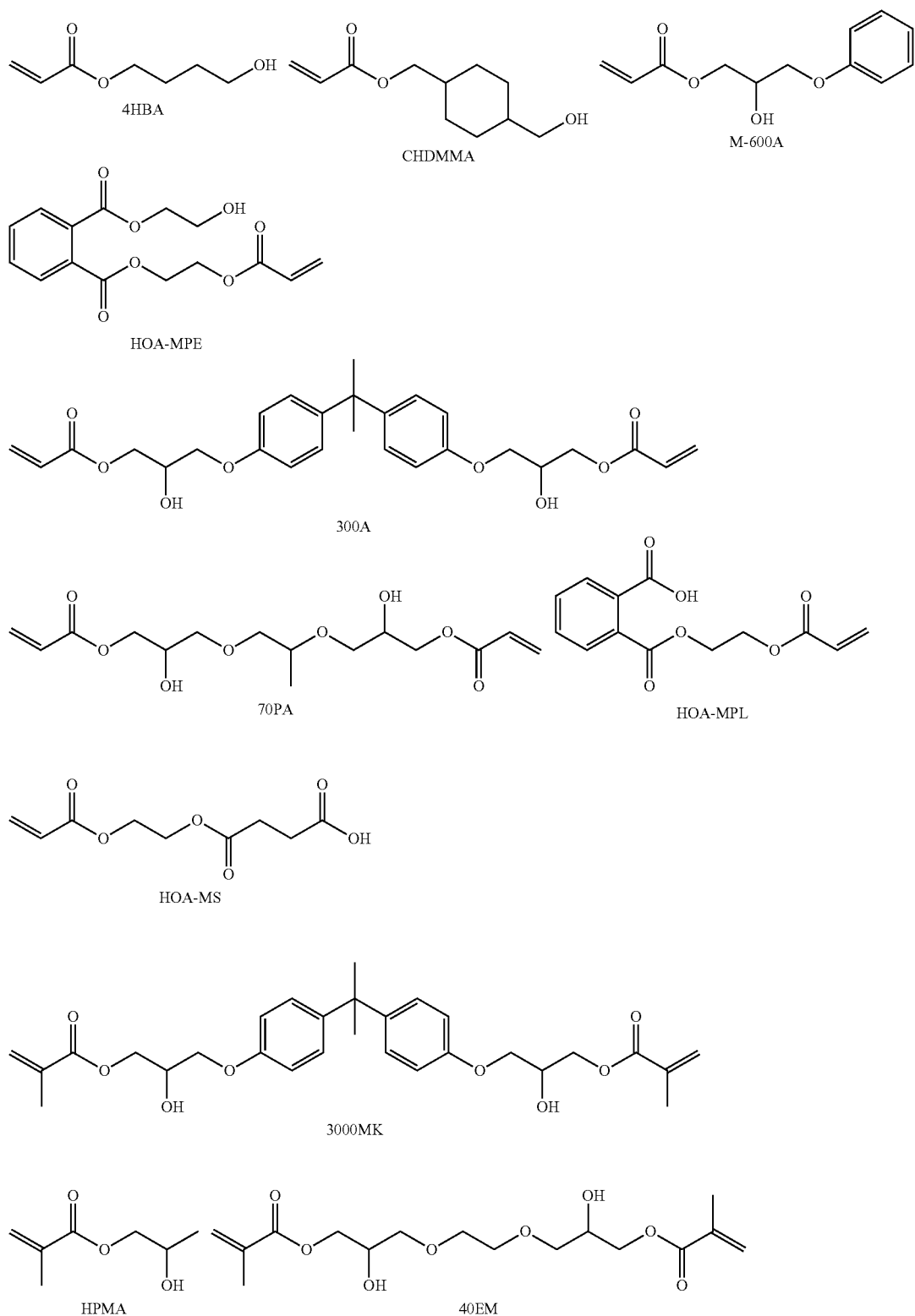

The respective structures of photopolymerization initiators listed in Tables 1 to 6 are as shown below.

In Tables 1 to 6, Irg 819 is "Irgacure 819" (an acylphosphine oxide compound) manufactured by BASF Japan Ltd.; Irg 184 is "Irgacure 184" (an alkylphenone compound) manufactured by BASF Japan Ltd.; and TPO is "Irgacure TPO" (an acylphosphine oxide compound) manufactured by BASF Japan Ltd.

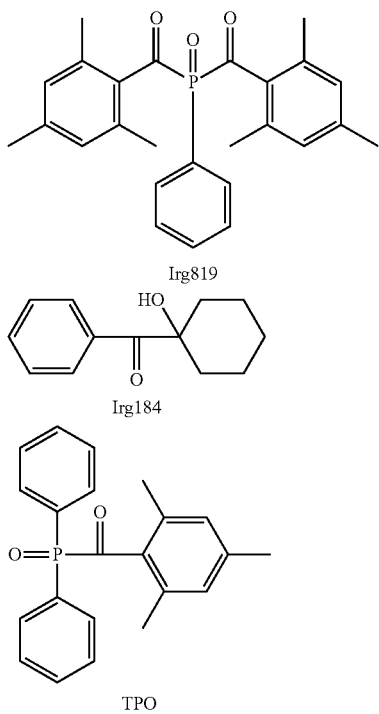

Irg819

Irg184

TPO

As shown in Tables 1 to 6, in each of Example 1 to 51, a photocurable composition which includes the (meth)acrylic monomer (X) and the (meth)acrylic monomer (H), and which has a functional group value (a) of from $0.50\times10^{-3}$ mol/g to $2.00\times10^{-3}$ mol/g, was used. As a result, it was possible to obtain a stereolithographed product which has an excellent flexural strength (specifically, 65 MPa or more), an excellent flexural modulus (specifically, 2,000 MPa or more), and an excellent fracture toughness (specifically, a total fracture work of 75 J/m² or more). Further, the photocurable compositions of Examples 1 to 51 had a viscosity suitable for stereolithography.

The above results confirmed that each of the photocurable compositions of Examples 1 to 51 is suitable for the production by stereolithography of a dental prosthesis or the like (a denture base, in particular).

As compared to Examples 1 to 51, Comparative Examples 1, 2, 4 to 7, and 9 in which the photocurable composition having a functional group value (a) of less than $0.50\times10^{-3}$ mol/g was used, the fracture toughness of each of the resulting stereolithographed products was reduced.

In addition, in Comparative Examples 3, 8, and 10, in which the photocurable composition having a functional group value (a) of greater than $2.00\times10^{-3}$ mol/g was used, the flexural strength and the flexural modulus of each of the resulting stereolithographed products was reduced.

The disclosures of Japanese Patent Application No. 2015-200394 filed on Oct. 8, 2015 is incorporated herein by reference in their entirety.

All publications, patent applications, and technical standards mentioned in the present specification are incorporated herein by reference to the same extent as if such individual publication, patent application, or technical standard was specifically and individually indicated to be incorporated by reference.

The invention claimed is:

1. A photocurable composition for use in stereolithography, the photocurable composition comprising:
   a (meth)acrylic monomer component comprising:
      a (meth)acrylic monomer (X) that is at least one selected from di(meth)acrylic monomers not containing, within one molecule, a hydroxyl group or a carboxy group and containing, within one molecule, two aromatic rings and two (meth)acryloyloxy groups, and that has a weight average molecular weight of from 400 to 580, and
      a (meth)acrylic monomer (H) that is at least one selected from (meth)acrylic monomers containing, within one molecule, at least one of a hydroxyl group or a carboxy group, and a (meth)acryloyloxy group, and that has a weight average molecular weight of from 100 to 700; and
   a photopolymerization initiator,
   wherein a functional group value (a) as defined by the following Formula (a) is from $0.50\times10^{-3}$ mol/g to $2.00\times10^{-3}$ mol/g:

functional group value $(a)=(n_H/M_H)\times P_H$  Formula (a)

wherein, in Formula (a), $n_H$ represents a total number of hydroxyl groups and carboxy groups contained in one molecule of the (meth)acrylic monomer (H); $M_H$ represents the weight average molecular weight of the (meth)acrylic monomer (H); and $P_H$ represents a mass ratio of the (meth)acrylic monomer (H) with respect to a total amount of the (meth)acrylic monomer component, a content of the acrylic monomer (H) is 350 parts by mass or less with respect to 1,000 parts by mass of a total content of the (meth)acrylic monomer component.

2. The photocurable composition according to claim 1, wherein at least one di(meth)acrylic monomer constituting the (meth)acrylic monomer (X) contains an ether bond within one molecule.

3. The photocurable composition according to claim 1, wherein at least one di(meth)acrylic monomer constituting the (meth)acrylic monomer (X) contains from one to four ether bonds within one molecule.

4. The photocurable composition according to claim 1, wherein at least one di(meth)acrylic monomer constituting the (meth)acrylic monomer (X) is a compound represented by the following Formula (x-1):

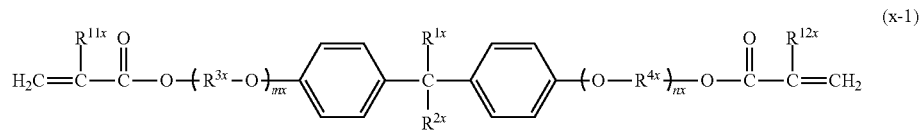

wherein, in Formula (x-1), each of $R^{1x}$, $R^{2x}$, $R^{11x}$, and $R^{12x}$ independently represents a hydrogen atom or a methyl group; each of $R^{3x}$ and $R^{4x}$ independently represents a straight chain or branched chain alkylene group having from 2 to 4 carbon atoms; and each of mx and nx independently represents a number from 0 to 4, and wherein mx and nx satisfy: $1\le(mx+nx)\le4$.

5. The photocurable composition according to claim 1, wherein at least one di(meth)acrylic monomer constituting the (meth)acrylic monomer (X) is a compound represented by the following Formula (x-2):

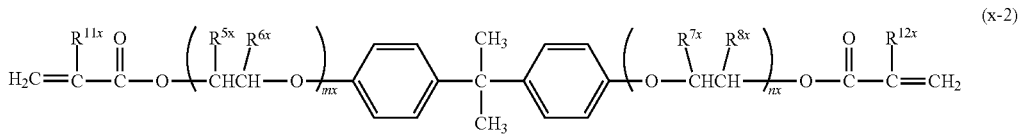

wherein, in Formula (x-2), each of $R^{5x}$, $R^{6x}$, $R^{7x}$, $R^{8x}$, $R^{11x}$, and $R^{12x}$ independently represents a hydrogen atom or a methyl group; and each of mx and nx independently represents a number from 0 to 4, and mx and nx satisfy: $1 \leq (mx+nx) \leq 4$.

6. The photocurable composition according to claim 1, wherein the (meth)acrylic monomer component further comprises at least one of:
- a (meth)acrylic monomer (A) that is at least one selected from di(meth)acrylic monomers not containing, within one molecule, a hydroxyl group, a carboxy group, or an aromatic ring and containing, within one molecule, one or more ether bonds and two (meth)acryloyloxy groups, and that has a weight average molecular weight of from 200 to 400,
- a (meth)acrylic monomer (B) that is at least one selected from (meth)acrylic monomers not containing, within one molecule, a hydroxyl group, a carboxy group, or an aromatic ring and containing, within one molecule, a ring structure other than an aromatic ring and one (meth)acryloyloxy group, and that has a weight average molecular weight of from 130 to 240,
- a (meth)acrylic monomer (C) that is at least one selected from di(meth)acrylic monomers not containing, within one molecule, a hydroxyl group, a carboxy group, an ether bond, or an aromatic ring and containing, within one molecule, a hydrocarbon skeleton and two (meth)acryloyloxy groups, and that has a weight average molecular weight of from 190 to 280, or
- a (meth)acrylic monomer (D) that is at least one selected from (meth)acrylic monomers not containing, within one molecule, a hydroxyl group or a carboxy group and containing, within one molecule, an aromatic ring and one (meth)acryloyloxy group, and that has a weight average molecular weight of from 160 to 400.

7. The photocurable composition according to claim 6, wherein:
- in the case that the (meth)acrylic monomer (A) is contained, at least one di(meth)acrylic monomer constituting the (meth)acrylic monomer (A) is a compound represented by the following Formula (a-1);
- in the case that the (meth)acrylic monomer (B) is contained, at least one (meth)acrylic monomer constituting the (meth)acrylic monomer (B) is a compound represented by the following Formula (b-1);
- in the case that the (meth)acrylic monomer (C) is contained, at least one di(meth)acrylic monomer constituting the (meth)acrylic monomer (C) is a compound represented by the following Formula (c-1); and
- in the case that the (meth)acrylic monomer (D) is contained, at least one (meth)acrylic monomer constituting the (meth)acrylic monomer (D) is a compound represented by the following Formula (d-1):

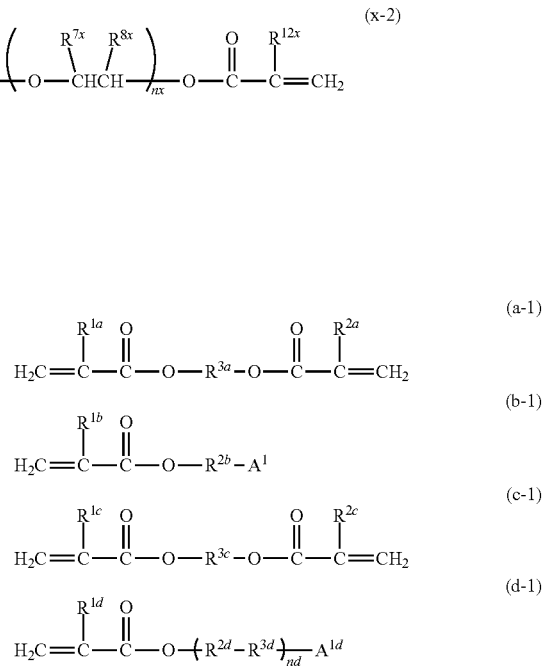

wherein,
- in Formula (a-1), each of $R^{1a}$ and $R^{2a}$ independently represents a hydrogen atom or a methyl group; each $R^{3a}$ independently represents a straight chain or branched chain alkylene group having from 2 to 4 carbon atoms; and p represents a number from 2 to 4;
- in Formula (b-1), $R^{1b}$ represents a hydrogen atom or a methyl group; $R^{2b}$ represents a single bond or a methylene group; and $A^1$ represents a ring structure other than an aromatic ring;
- in Formula (c-1), each of $R^{1c}$ and $R^{2c}$ independently represents a hydrogen atom or a methyl group; and $R^{3c}$ represents an alkylene group having from 1 to 9 carbon atoms; and
- in Formula (d-1), $R^{1d}$ represents a hydrogen atom or a methyl group; each $R^{2d}$ independently represents a straight chain or branched chain alkylene group having from 1 to 5 carbon atoms; each $R^{3d}$ independently represents a single bond, an ether bond (—O—), an ester bond (—O—(C=O)—), or —$C_6H_4$—O—; $A^{1d}$ represents an aromatic ring; and nd represents a number from 1 to 2.

8. The photocurable composition according to claim 6, wherein:
- in the case that the (meth)acrylic monomer (A) is contained, at least one di(meth)acrylic monomer constituting the (meth)acrylic monomer (A) is a compound represented by the following Formula (a-2);
- in the case that the (meth)acrylic monomer (B) is contained, at least one (meth)acrylic monomer constituting the (meth)acrylic monomer (B) is a compound represented by the following Formula (b-2);

in the case that the (meth)acrylic monomer (C) is contained, at least one di(meth)acrylic monomer constituting the (meth)acrylic monomer (C) is a compound represented by the following Formula (c-2); and in the case that the (meth)acrylic monomer (D) is contained, at least one (meth)acrylic monomer constituting the (meth)acrylic monomer (D) is a compound represented by the following Formula (d-2):

monomer (A), the (meth)acrylic monomer (B), the (meth)acrylic monomer (C), or the (meth)acrylic monomer (D) is contained, a total content of the (meth)acrylic monomer (A), the (meth)acrylic monomer (B), the (meth)acrylic monomer (C) and the (meth)acrylic monomer (D) is from 30 parts by mass to 750 parts by mass with respect to 1,000 parts by mass of a total content of the (meth)acrylic monomer component.

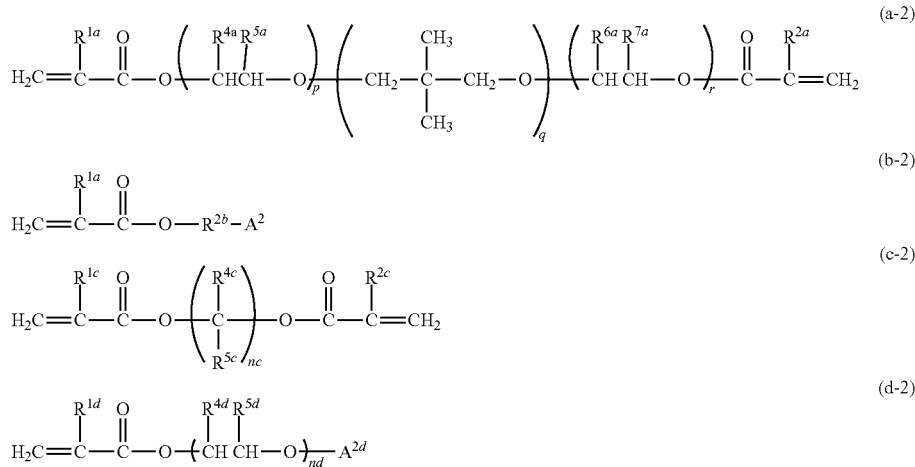

wherein, in Formula (a-2), each of $R^{1a}$, $R^{2a}$, $R^{4a}$, $R^{5a}$, $R^{6a}$, and $R^{7a}$ independently represents a hydrogen atom or a methyl group; and each of p, q, and r independently represents 0 or 1, and wherein p, q, and r satisfy: $p+q+r \geq 2$;

in Formula (b-2), $R^{1b}$ represents a hydrogen atom or a methyl group; $R^{2b}$ represents a single bond or a methylene group; and $A^2$ represents a ring structure containing a dicyclopentenyl skeleton, a dicyclopentanyl skeleton, a cyclohexane skeleton, a tetrahydrofuran skeleton, a morpholine skeleton, an isobornyl skeleton, a norbornyl skeleton, a dioxolane skeleton, or a dioxane skeleton;

in Formula (c-2), each of $R^{1c}$ and $R^{2c}$ independently represents a hydrogen atom or a methyl group; each of $R^{4c}$ and $R^{5c}$ independently represents a hydrogen atom or a methyl group; and nc represents a number from 1 to 9, and wherein an alkylene group represented by $-(CR^{4c}R^{5c})_{nc}-$ has from 1 to 9 carbon atoms; and in Formula (d-2), each of $R^{1d}$, $R^{4d}$ and $R^{5d}$ independently represents a hydrogen atom or a methyl group; $A^{2d}$ represents an aromatic ring; and nd represents a number from 1 to 2.

9. The photocurable composition according to claim 1, wherein a content of the acrylic monomer (X) is 100 parts by mass or more with respect to 1,000 parts by mass of a total content of the (meth)acrylic monomer component.

10. The photocurable composition according to claim 1, wherein a content of the acrylic monomer (H) is from 60 parts by mass to 480 parts by mass with respect to 1,000 parts by mass of a total content of the (meth)acrylic monomer component.

11. The photocurable composition according to claim 6, wherein, in the case that at least one of the (meth)acrylic 12. The photocurable composition according to claim 1, wherein the photopolymerization initiator is at least one selected from alkylphenone compounds or acylphosphine oxide compounds.

13. The photocurable composition according to claim 1, wherein a content of the photopolymerization initiator is from 1 part by mass to 50 parts by mass with respect to 1,000 parts by mass of a total content of the (meth)acrylic monomer component.

14. The photocurable composition according to claim 1, wherein the photocurable composition has a viscosity, as measured using a Type E viscometer at 25° C. and 50 rpm, of from 20 mPa·s to 1500 mPa·s.

15. The photocurable composition according to claim 1, wherein the photocurable composition is used for production, by stereolithography, of a dental prosthesis, a medical device for intraoral use, or a tooth and jaw model.

16. The photocurable composition according to claim 1, wherein the photocurable composition is used for production, by stereolithography, of a denture base or a mouthpiece.

17. The photocurable composition according to claim 1, wherein the photocurable composition is used for production, by stereolithography, of a denture base.

18. A denture base that is a cured product of the photocurable composition according to claim 17.

19. A plate denture comprising the denture base according to claim 18 and an artificial tooth fixed to the denture base.

20. The photocurable composition according to claim 1, wherein a content of the acrylic monomer (X) is 400 parts by mass or more with respect to 1,000 parts by mass of a total content of the (meth)acrylic monomer component and the content of the content of the acrylic monomer (H) is from 80 parts by mass to 350 parts by mass with respect to 1,000 parts by mass of the total content of the (meth)acrylic monomer component.

21. The photocurable composition according to claim 1, wherein a total content of the (meth)acrylic monomer (X) and the (meth)acrylic monomer (H) in the (meth)acrylic monomer component is 50% by mass or more with respect to the total amount of the (meth)acrylic monomer component.

* * * * *